Figure 1:
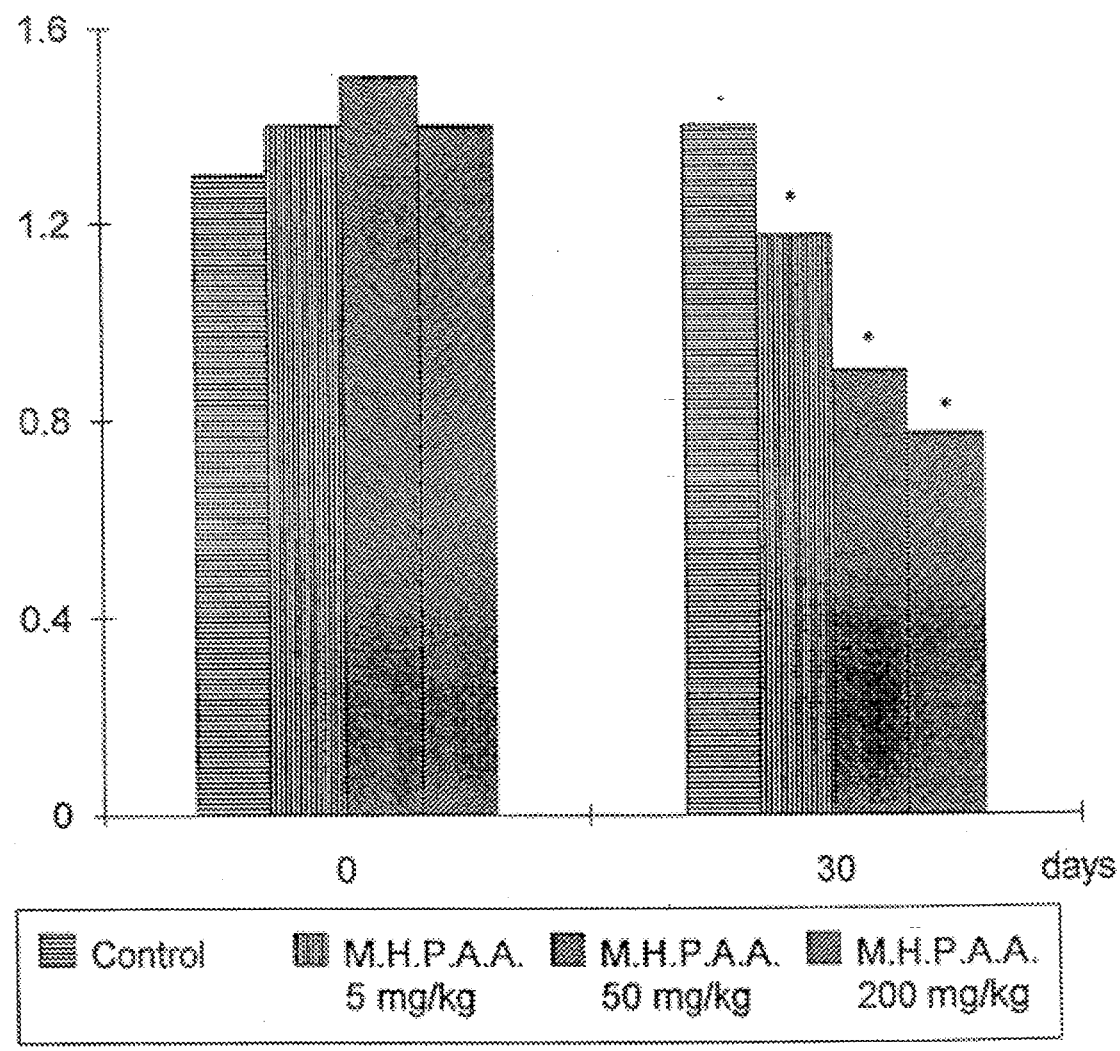

United States Patent [19]

Granja et al.

[11] Patent Number: 5,663,156
[45] Date of Patent: Sep. 2, 1997

[54] MIXTURE OF HIGHER PRIMARY ALIPHATIC ALCOHOLS, ITS OBTENTION FROM SUGAR CANE WAX AND ITS PHARMACEUTICAL USES

[75] Inventors: Abilio Laguna Granja; Juan Magraner Hernandez; Daisy Carbajal Quintana; Lourdes Arruzazabala Valmana; Rosa Mas Ferreiro; Milagros Garcia Mesa, all of La Habana, Cuba

[73] Assignees: Laboratorios Dalmer SA, La Habana, Cuba; Adanifer, S.A., Fribourg, Switzerland

[21] Appl. No.: 211,501

[22] PCT Filed: Feb. 25, 1993

[86] PCT No.: PCT/EP93/00007

§ 371 Date: Jul. 25, 1994

§ 102(e) Date: Jul. 25, 1994

[87] PCT Pub. No.: WO94/07830

PCT Pub. Date: Apr. 14, 1994

[30] Foreign Application Priority Data

Sep. 29, 1992 [CU] Cuba ............................... 107/92

[51] Int. Cl.$^6$ ..................... C07C 29/74; A61K 31/045
[52] U.S. Cl. .................. 514/164; 514/724; 568/840; 568/877; 568/920; 568/921; 568/923
[58] Field of Search .................... 568/923, 840, 568/877, 920, 921; 514/724, 164

[56] References Cited

U.S. PATENT DOCUMENTS

| 2,021,926 | 11/1935 | Sexton et al. | 568/877 |
| 2,719,858 | 10/1955 | Hill | 568/923 |
| 3,031,376 | 4/1962 | Levin et al. | 514/724 |
| 4,186,212 | 1/1980 | Howell | 514/724 |
| 5,106,879 | 4/1992 | Clark | 514/724 |
| 5,159,124 | 10/1992 | Bertholet | 568/877 |
| 5,166,219 | 11/1992 | Katz | 514/724 |

FOREIGN PATENT DOCUMENTS

| 0488928A2 | 6/1992 | European Pat. Off. | |
| 2159194 | 6/1973 | France | 514/164 |
| 650367 | 2/1951 | United Kingdom | 514/164 |
| 2105699 | 3/1983 | United Kingdom | 568/877 |

Primary Examiner—C. Warren Ivy
Assistant Examiner—Lyman H. Smith
Attorney, Agent, or Firm—Lorusso & Loud

[57] ABSTRACT

A mixture of higher primary aliphatic alcohols of 22 to 38 carbon atoms can be obtained by saponifying and extracting steps with organic solvents from sugar cane wax. The mixture which contains tetracosanol, hexacosanol, heptacosanol, octacosanol, nonacosanol, triacontanol, dotriacontanol and tetratriacontanol can be used for the treatment of hypercholesterolemia, and atherosclerotic complications as platelet hyperaggregabiulity, ischemia and thrombosis, and prevents drug induced gastric ulcer and improves male sexual activity.

20 Claims, 19 Drawing Sheets

MIXTURE OF HIGHER PRIMARY ALIPHATIC ALCOHOLS, ITS OBTENTION FROM SUGAR CANE WAX AND ITS PHARMACEUTICAL USES

This application is a 35 U.S.C. 371 National Stage filing of PCT/EP93/00007 published as WO 94/07830 on Apr. 14 1994.

This invention is related to a mixture of higher primary aliphatic alcohols, containing alcohols of a range from 24 to 34 carbon atoms and more especially, those with straight chain of 24, 26, 27, 28, 29, 30, 32 and 34 carbon atoms.

This mixture shows a relative composition of each alcohol, that is highly reproducible batch to batch.

According with the present invention this mixture of higher primary aliphatic alcohols from 24 to 34 carbon atoms (thereafter called M.H.P.A.A.), in a relative narrow quantitative correlation, shows new properties such as antiplatelet, antithrombotic and/or anti-isquemic agents, as well as for the antagonism of drug-induced ulcers and that is why this specific mixture can be used as active ingredient of pharmaceutical formulations prepared for these purposes.

An object of the invention is to place at the public's disposal M.H.P.A.A. of 24 to 34 carbon atoms for pharmaceutical formulations.

One of the objects of this invention is to obtain, isolate and purify this, particular, mixture of higher primary aliphatic alcohols (M.H.P.A.A.) of 24 to 34 carbon atoms from the sugar cane wax, both from raw and refined wax.

Lipid-lowering effects of sugar cane wax have been demonstrated in rats (Fukuda, Effects of sugar cane wax on serum liver lipids on rats; Chemical Abstracts, 106, 17, 137413p) and mice (Sho H. et al (1984; Effects of Okinawan sugar cane wax and fatty alcohols on serum and liver lipids in the rats; J. Nutri. Vitaminol 30 (6) 553–559).

Firstly, effects of sugar cane wax on serum and liver lipids were investigated in male Wistar rats fed high levels of plants and animal fats. The authors found that addition of 0.5% of sugar cane wax to dietary fat reduces significantly serum triglycerides in rats fed plant or animal fats, but only in the last ones cholesterol levels decreased significantly, without affecting the content of liver lipids. Hence, authors concluded that sugar cane wax shows hypolipidemic effects.

On the other hand, Sho H. et al (1984) studied the effects of Okinawan sugar cane wax on serum and liver lipids in rats fed a diet containing 0.5% of this wax and they found a significant reduction of both serum and liver cholesterol content. Nevertheless, no significant variation in cholesterol levels were found when used fatty alcohols from the same wax in the diet of animals. Thus, they discarded that lipid-lowering properties of the wax were attributable to these alcohols.

However, some years later, Shimura S., Hagesawa T., Takano S. and Susuki T. (1987: Studies on the effect of octacosanol on the motor endurance in mice; Nutrition Reports Int. 36, 1029–1038) studied the effects of octacosanol in mice subjected to physical activity and fed octacosanol-enriched diet. They found that octacosanol isolated from sugar cane wax significantly reduced the content of both triglycerides and cholesterol in the liver, while only serum levels of triglycerides were reduced in a significant manner. They concluded that octacosanol isolated from sugar cane wax showed lipid-lowering properties, which disagrees with the previous results of Sho H. et al (1984) aforementioned.

Likewise, antilipaemic effects have been also further attributed to hexacosanol, another higher primary aliphatic alcohol, although very high doses were reported as needed to obtain such results (10–30 mg/kg/day) (Hagiwara Y. 1987: Antilipaemic agents containing hexacosanol used to treat hypertension, arteriosclerosis, diabetes mellitus, heart disease and obesity; JP A 62 099323).

There are different commercial lipid-lowering drugs considered as effective, safe and well tolerated, but most of them produce different adverse side effects. Since lipid-lowering therapy must be administered chronically, this aspect is very important.

For example, gemfibrozil reduces serum triglycerides, raises HDL-C levels and produces a mild decrease of serum cholesterol, but several drug-related adverse effects have been reported. Thus, gastrointestinal effects such as epigastric pain, diarrhoea, nausea, vomiting and flatulence have been referred. Moreover, headache, dizziness, blurred vision, impotence, decreased libido and liver function abnormalities such as increased transaminases, LDH, creatinphosphokinase and alkaline phosphatase have occurred in gemfibrozil-treated patients. Likewise, it should not be administered to patients with renal failures.

Probucol is other lipid-lowering drug with antioxidant properties that causes mild decreases of serum cholesterol and LDL-C. Nevertheless, a disadvantage of its lipid-lowering action is that it reduces the HDL-C fraction. Moreover, several adverse effects as gastrointestinal disturbances in approximately 10% of the population, as well has a considerable variation in the electrocardiogram have been reported.

Other lipid-lowering drugs used frequently are Cholestiramine and Cholestipol. These are effective first-line cholesterol-lowering drugs that strongly decrease serum cholesterol and LDL-C, but tend to increase triglyceride levels. These drugs induced several gastrointestinal symptoms, mainly constipation. Compliance with the treatment is generally low, because the adverse symptoms and since they are not easy-to-take agents, requiring doses up to 12 to 20 g/day to achieve the desired effects. Moreover, adverse chemical interactions with other drugs such as digitoxin have been described.

Lovastatin is the first of the "statins", drugs acting as inhibitors of HMGCoA-reductase and thus efficiently reducing serum cholesterol and LDL-C levels, it also moderately increases HDL-C and decreases triglycerides. Several adverse effects have been reported for this drug. Thus, the main adverse effects are miopathy, mild to moderate increases of creatinphosphokinase and persistent increases in serum transaminases, that frequently becames reversible after withdrawal of the treatment. Miopathy has occurred mainly in patients receiving concomitant therapy with inmunosuppresive drugs as gemfibrozil or niacin. Moreover, adverse effects such as skin rash, pruritus, headache and severe muscular lesions in sensitive patients resulting in myolisis have also been reported by lovastatin-treated patients. Moreover, drug-related occurrence of testicular atrophy and hepatic tumors in laboratory animals has been also reported.

Similar, simvastatin and pravastatin are other "statins", acting by the same mechanism of lovastatin and showing approximately the same cholesterol-lowering effects. Adverse effects reported by these patients are similar to those reported for lovastatin-treated patients, but claimed as slightly lower. Simvastatin and pravastatin-treated patients showed increases of transaminases and creatin phosphokinase and patients reported constipation, flatulence, nausea, headache, fatigue, subcutaneous rash and myopathies.

Table 1 shows the qualitative and quantitative composition of the mixture of M.H.P.A.A. obtained from sugar cane wax according to the invention.

TABLE 1

General qualitative and quantitative composition of the M.H.P.A.A. used in the formulations.

| Components | Proportion in the mixture |
|---|---|
| 1 - tetracosanol | 0.5–5.0% |
| 1 - hexacosanol | 5.0–15.0% |
| 1 - heptacosanol | 0.5–5.0% |
| 1 - octacosanol | 50.0–80.0% |
| 1 - nonacosanol | 0.5–3.0% |
| 1 - triacontanol | 6.0–20.0% |
| 1 - dotriacontanol | 1.0–10.0% |
| 1 - tetratriacontanol | 0.0–2.5% |

The specific alcohol mixture proposed in the present invention shows the qualitative and quantitative composition between its components described in Table 2.

TABLE 2

Especial qualitative and quantitative composition of M.H.P.A.A. proposed in the present invention

| Components | Proportion in the mixture |
|---|---|
| 1 - tetracosanol | 0.5–1.0% |
| 1 - hexacosanol | 6.0–8.0% |
| 1 - heptacosanol | 2.5–3.5% |
| 1 - octacosanol | 60.0–70.0% |
| 1 - nonacosanol | 0.5–1.0% |
| 1 - triacontanol | 10.0–15.0% |
| 1 - dotriacontanol | 4.5–6.0% |
| 1 - tetratriacontanol | 0.5–2.0% |

This composition shows, surprisingly, new effects such as antiplatelet, anti-thrombotic and/or anti-isquemic agents, as well as for the antagonism of drug-induced ulcers. This particular mixture shows also the same properties reported for the mixture described in the European Patent Application 0 488 928.

Still another object of the invention is to demonstrate the protective effect of M.H.P.A.A. on ischemia.

Still another object of the invention is to demonstrate that M.H.P.A.A. shows pharmacological interaction with ASA, the drug most commonly used for cerebral ischemic therapy. Thus, results showed a synergism between antiplatelet, anti-thrombotic and anti-ischemic properties of M.H.P.A.A. and ASA.

Still another object of the present invention is demonstrate that M.H.P.A.A. reduced significantly the gastric ulcera induced by aspirin, ethanol, indomethacine, compound C4880 (Sigma) and other medications producing gastric ulcer in human beings under treatment.

It has been described that gastric ulcer induced by alcohol is mainly related with an increase of TxA2 as physiological agent, while ulcer induced by C4880 mainly involves serotonergic mechanisms, although a role of TxA2 in its ethiogenesis can not be ruled out. On the other hand, gastric ulcer induced by ASA is related with the inhibition of prostaglandins (E series) synthesis produced by ASA, since they have a cytoprotective effect ion the gastric mucosa. It has been demonstrated that the TxA2 to pgI2 ratio in gastric mucosa plays an important role as an endogenous mechanism of its integrity.

On the other hand, it has been described that treatment with some lipid-lowering drugs reduces the tendency to platelet hyperaggregation frequently seen in the hyperlipidemic patients and experimental data have shown antiaggregatory effects mediated by these compounds. Nevertheless, only some cholesterol-lowering drugs show this property. As has been referred, atherosclerosis is a variable combination of changes of the intima of the arteries consisting of the focal accumulation of lipids, complex carbohydrates, blood and blood products, fibrous tissue and calcium deposits, frequently also associated with medial changes. Thus, this definition indicates atherosclerosis as a multifactorial process, not only including hyperlipidaemia as risk factor.

Thus, between factors contributing to atherosclerosis development platelet aggregation has a very important place. Platelet releasing granule contents activating arachidonic acid, which metabolizes into cyclic endoperoxides. These are mainly transformed into cyclic endoperoxides and finally rendering thromboxane A2 (TxA2), a strong vascular vasoconstrictor and platelet aggregatory agent. Platelet aggregation can be elicited by different compounds, such as collagen, ADP and epinephrine, between others. Thus, different experimental "in vivo", "ex vivo" or "in vitro" models testing effectiveness of putative antiplatelet drugs commonly explored their effect on platelet aggregation induced by these agents.

These tests are also used for testing platelet aggregation in healthy volunteers and in patients with diseases frequently inducing hyperaggregability, such as hypercholesterolemia and diabetes, between others. Between these tests, collagen-induced platelet aggregation is one of the most frequently used. Thus, as example, collagen injected endovenously leads to reversible intravascular platelet aggregation "in vivo" and aggregates of platelets enter to the vascular microcirculation, subsequently decreasing the count of circulating platelet and simultaneously increasing the plasma MDA concentration. Moreover, in some species this injection of collagen induces mortality produced by thrombosis. In these models, antiplatelet drugs generally prevents the decrease of platelet content and increase of MDA concentration, as well as the collagen induced mortality.

Some drugs showing platelet anti-aggregatory effects are useful for treatment of thrombotic diseases, myocardial infarction and stroke, but not all of them show these advantages. On the other hand, there are antithrombotic drugs that mainly acting by lytic processes affecting blood coagulation, but not on the platelet aggregation such as estreptokinase and urokinase.

Since ischemic cardiovascular diseases, stroke and vascular peripheric obstructive pathologies are the main sequelae of atherosclerosis, effects of several drugs on these complications are commonly tested. Thus, theoretically a drug showing cholesterol-lowering properties that also can prevent these complications by acting on other events involved in these processes must be advantageous for treating these patients. Likewise, reduction of TxA2 levels have been associated not only with antiplatelet and antithrombotic effects, but also with antiischemic effects. The pharmacological screening of antiischemic drugs commonly includes the evaluation of their effects on brain-induced global ischemia. Thus, it has been described the protective effect of different drugs on rat cerebral ischemia for certain nonsteroidal anti-inflamatory drugs (NSAID) which inhibits reactions catalyzed by ciclooxygenase, as well as specific inhibitors of thromboxane synthetase and prostacyclin analogues (PgI2) (Borzeix MG and Cahn J; 1988; Effects of new chemically metabolically stable prostacyclin analogues on early consequences of a transient cerebral oligemia in rats; Prostaglandins 35, 5, 653–664).

Other experimental models, such as global ischemia induced experimentally in Mongolian gerbils are also used frequently.

Acetylsalicylic acid (ASA) is a compound exhibiting antiplatelet, antithrombotic and anti-ischemic properties in experimental models and human beings. It is the drug most widely used for treatment of acute myocardial infarction and stroke, as well as for prevent thromboembolic disorders. ASA effects are supported by its well known inhibition of cyclooxygenase, a key enzyme on the arachidonic acid metabolism. Thus, ASA induces a significant and remarkable reduction of serum levels of thromboxane A2 (TxA2) a recognized patophysiological agent for the vascular endothelium and it explains the aforementionend effects of ASA.

Nevertheless, since the ASA inhibition is exerted cyclooxygenase level, not only TxA2 levels are reduced, but also levels of prostacyclin (PgI2) a compound with pharmacological properties opposite of that showed by TxB2. On the other hand, taking into account that ASA inhibits the synthesis of prostaglandins (series E), it induces gastric damages because it prevents the cytoprotective effects of prostaglandins. This is the basis of the main adverse side effect reported for ASA, that is, gastritis, gastric ulcera and related disturbances.

A preferent composition of the specific higher primary aliphatic alcohols reffered in the present invention is the one described in Table 3.

TABLE 3

More especial qualitative and quantitative composition of M.H.P.A.A. used in the formulations

| Components | Proportion in the mixture |
| --- | --- |
| 1 - tetracosanol | 0.8 +/− 0.1% |
| 1 - hexacosanol | 6.7 +/− 0.3% |
| 1 - heptacosanol | 3.0 +/− 0.3% |
| 1 - octacosanol | 65.6 +/− 3.4% |
| 1 - nonacosanol | 0.7 +/− 0.1% |
| 1 - triacontanol | 12.5 +/− 0.6% |
| 1 - dotriacontanol | 5.0 +/− 0.4% |
| 1 - tetratriacontanol | 0.8 +/− 0.1% |

The pharmaceutical formulations with this specific mixture of higher primary aliphatic alcohols, may be administered to human and animals beings. The daily dosage of M.H.P.A.A. obtained from sugar cane wax to be used for treatment of different diseases is established between 1 to 100 mg per day, preferably about 3–20 mg M.H.P.A.A. may e.g. be administered orally or parenterally. A preferred route of administration is oral film-coated tablets as well as granules or capsules.

Pharmaceutical formulations contains as an active ingredient from 0.5 to 15.0% wt of M.H.P.A.A. This dosage is obtained by mixing M.H.P.A.A. with different excipients such as agglutinants, disintegrators, lubricants, sliders or just fillers. In these excipients are included lactose, corn starch, saccharose, magnesium stearate, microcrystalline cellulose, sodium croscarmellose gelatin, cellulose acetophtalate, titanium dioxide, special talc for tablets and polyethylenglycol.

An object of the present invention is the mixture of acetyl salicylic acid with the M.H.P.A.A., as a pharmacological agent with antiplatelet, anti-thrombotic and anti-isquemic properties when the ratio between them is from 20:1 to 1:20, especially those in ratio 10:1 to 1:10.

Sugar cane wax and its natural source, mud, have always been a matter of interest, not only because of their industrial application, but also because of their chemical composition. The amount of wax in sugar cane ranges between 0.1% to 0.3%, depending on its variety. During the agroindustrial process, only 40% of the wax content is diluted in the juice, the remaining material is lost in the bagasse.

From this 40%, the 95% of it, is absorbed by the mud, from which raw wax is obtained. This wax is made up of esters, aldehydes, ketones hydrocarbons, fatty acids and free alcohols, the amount of each depending on the variety and origin of the sugar cane plant and the technology used to obtain the wax.

The straight chain aliphatic alcohols obtained from sugar cane byproducts have been studied by several authors to learn about their composition and main features. The obtention of different groups of compounds from all kinds of waxes has been reported (J. A. Lamberton et al, 1959; Australian Journal of Chemistry 13, 261–268 and Horn A. and Martic JS; 1957; Journal of Science Food and Agriculture 10, 571) suggest a method for obtaining fatty alcohols from sugar cane cuticular wax based on the homogeneous saponification with alcoholic potassium hydroxide, following by the esterification of the unsaponifiable material and further molecular distillation.

It is also reported another method to isolate the alcohol mixture through a high efficiency high vacuum column. The high vacuum wax distillation for the chemical isolation of carbonylic compounds and the extraction of the remaining wax, using petrol ether. The solvent evaporates and the remaining content is acetylated for its further isolation through alumina chromatography. Finally, through alkaline hydrolysis alcohols are obtained and then recrystallized in ethanol, showing a fusion point ranging from 80° to 82° C.

A procedure for obtaining the mixture of higher aliphatic primary alcohols from animal and vegetable wax, is based on the saponification of the fatty esters followed by the extraction of alcohol mixtures through a fluid in sub and supercritical state of between 25°–100° C. using adequate solvents, showing that depending on the solubility and at low temperature and pressure changes, selective extraction can be carried out. According to this procedure applied to the sugar cane wax, it is possible to obtain 5% of $C_{20}$–$C_{36}$ alcohol mixtures.

Other project (Inada S, Furukawa K., Masui T., Honda K., Ogasawara J. and Tsubikamoto G.; 1986; Process for recovering primary normal aliphatic higher alcohols JP 60-119514) proposed a very similar extraction method applied to waxes, that is based on fluids in sub and supercritical states of $CO_2$ with ethylene. The separation of organic compounds from their mixtures by means of fluids in sub and supercritical states is also described. From the analytical point of view, all these are valuable methods, but high scale implementation is hindered by the use of column chromatography and molecular distillation, which are all not economic procedures.

The procedure of the current invention is based on a homogeneous phase saponification process of the sugar cane wax previously melted with concentrated solutions of alkaline and alkaline terrum hydroxides, especially with that of low molecular weight and more especially with that of sodium, potassium and calcium.

The concentration of the hydroxide solutions must be such that the ratio in weight of the corresponding hydroxide with that of the wax to be processed must be over 5% on, especially from 8 to 25% and more especially, from 15 to 25%. The saponification process remains for a period of 30 minutes on and more especially from 2 to 5 hours. The solid obtained in this step is taken to a solid-liquid extractor, where M.H.P.A.A. is selectively extracted with adequate organic solvents, choosen among ketones from 3 to 8 carbon atoms, alcohols from 1 to 5 carbon atoms, hydrocarbons from 6 to 9 carbon atoms, haloforms as well as aromatic compounds such as benzene and it derivatives including mixtures of them. Some of the solvents used in the present invention are the following: acetone, methyl ethyl ketone, pentanone, hexanone, heptanone, 2-methylpentanone, ethanol, methanol, 2-propanol, butanol, terbutanol, pentane, hexane, heptane, octane, chloroform, 1,2 dichloroethane, dichloromethane, trichloroethane, 1,2,3-trichloropropane, benzene, toluene, phenol, p-methyl toluene and others.

The extraction is carried out in periods ranging between 5 to 10 h. Afterwards,the product is successively crystallized using the above mentioned solvents or their mixtures. The yield attained ranges about 30%, while the purity of M.H.P.A.A. attained ranges from 80 to 98% and more especially from 90 to 98%. M.H.P.A.A. thus obtained is formed by alcohols ranging from 22 to 38 carbon atoms. This is an off-white color mixture with a fusion point between 76.5 and 84.5° C. For the analysis of M.H.P.A.A. through gas chromatography in fused silica capillary column, these are derivatized by means of N methyl-N-TMS-trifluoroacetamide (MSTFA).

The proposed procedure for obtaining M.H.P.A.A. from sugar cane wax has some advantages with regards to other previously reported. One of these advantages is related with the short obtention time. Other advantage of this invention is related with the practical yields (near 30% in weight) that can be obtained of alcohols from the sugar cane wax compared with the results previously described of Sho et al, which reports yields lower than 5%. Other advantage of the proposed procedure is related with the purity degree of M.H.P.A.A. that can be obtained (near 98% which are significantly higher from that reported in the previously reported works. Thus, the method that has been proposed in the present invention is simple and appropiate for large scale production compared with that reported by Inada et al (JP 60-119514) and also by Hagiwara Y. (JP 62-87537).

Finally, in a whole picture of M.H.P.A.A. profile, its very good safety and tolerability represent an important advantage compared with the drugs of the state of art. Thus, results obtained in acute, subchronic and chronic studies conducted in rodents, rabbits, Beagle dogs and monkeys showed no drug-related toxicity. Moreover, it does not show any mutagenic effect or has teratogenic effects in rabbits or rats. M.H.P.A.A. adminstration over two generations did not affect fetal development nor reproductive performance in rats. Finally, a 24 months carcinogenecity study conducted in rats also showed the lack of toxicity and carcinogenic effects of M.H.P.A.A.

Short and long-term clinical trials also support the excellent safety and tolerability of the treatment.

The objects and purposes of the present invention shall be described in detail in the following examples. The examples shall not be limiting the scope of the said invention.

EXAMPLE 1

1000 g of refined wax from sugar cane are taken to be melted at 100°–110° C., adding 200 g of potassium hydroxide dissolved in 150 mL of water. This process is maintained for 5 h with stirring. M.H.P.A.A. is extracted from the solid obtained in the process for 12 h in a solid-liquid extraction system using heptane as solvent. The extract obtained is cooled at room temperature, whereby M.H.P.A.A. is crystallized and recrystallized in methyl ethyl ketone. As much as 285 g of this alcohol mixture were obtained with apurity amounting to 94.70%. The melting point of the mixture ranges from 80.5° to 82.5° C. Table 4 shows the qualitative and quantitative composition of M.H.P.A.A. obtained using this procedure.

TABLE 4

Qualitative and quantitative compositon of M.H.P.A.A. obtained

| Component | Percentage of each alcohol |
|---|---|
| 1 - tetracosanol | 0.81 |
| 1 - hexacosanol | 7.00 |
| 1 - heptacosanol | 2.81 |
| 1 - octacosanol | 65.09 |
| 1 - nonacosanol | 0.67 |
| 1 - triacontanol | 12.43 |
| 1 - dotriacontanol | 5.05 |
| 1 - tetratriacontanol | 0.84 |

EXAMPLE 2

Two (2) kg of raw wax from sugar cane are taken to be melted at 85°–100° C., to which 300 g of sodium hydroxide dissolved in 200 ml of water are added, the saponification process remains for a period of 4 h with stirring. The extraction of M.H.P.A.A. is implemented using chloroform as solvent for a period of 10 hours in a conventional solid-liquid extraction system, whereby the extract obtained is cooled at room temperature, the solid obtained is recrystallized in methanol and finally in a chloroform/methyl ethyl ketone mixture. M.H.P.A.A. (405 g) was obtained with a purity amounting to 92.52%. M.H.P.A.A. melting point ranges from 79.0°–80.5° C. Table 5 shows the qualitative and quantitative composition of M.H.P.A.A. obtained using this procedure.

TABLE 5

Qualitative and quantitative composition of M.H.P.A.A. obtained

| Component | Percentage of each alcohol |
|---|---|
| 1 - tetracosanol | 0.87 |
| 1 - hexacosanol | 6.84 |
| 1 - heptacosanol | 3.08 |
| 1 - octacosanol | 62.92 |
| 1 - nonacosanol | 0.80 |
| 1 - triacontanol | 12.66 |
| 1 - dotriacontanol | 4.65 |
| 1 - tetratriacontanol | 0.70 |

EXAMPLE 3

Twelve kg of calcium hydroxide dissolved in 7 L of water are added to 50 kg of refined sugar cane wax—previously melted at 100°–120° C. The saponification process is continued for 7.5 hours with stirring. M.H.P.A.A. is extracted using ethanol as solvent for 12 hours in a solid-liquid extraction system. The obtained extract is left to cool at room temperature, later this solid is recrystallized in chloroform M.H.P.A.A. (13.7 kg) obtained with a purity of 93.77%. The melting point of the mixture ranges from 80.0°–82.0° C. Table 6 shows the qualitative and quantitative composition of M.H.P.A.A. obtained using this procedure.

TABLE 6

Qualitative and quantitative composition of

M.H.P.A.A. obtained

| Component | Percentage of each alcohol |
|---|---|
| 1 - tetracosanol | 0.71 |
| 1 - hexacosanol | 6.88 |
| 1 - heptacosanol | 3.06 |
| 1 - octacosanol | 64.70 |
| 1 - nonacosanol | 0.62 |
| 1 - triacontanol | 12.01 |
| 1 - dotriacontanol | 5.09 |
| 1 - tetratriacontanol | 0.90 |

EXAMPLE 4

8.6 kg of calcium hydroxide dissolved in 4.5 l of water are added to 50 kg of raw sugar cane wax, previously melted at 100°–120° C. The saponification process is done with continuous stirring for 3 h. M.H.P.A.A. is extracted with dichloromethane as solvent for 12 h in a solid-liquid extractor. The product obtained is left to cool at room temperature and the solid obtained is recrystallized in a mixture of hexane and acetone 1:1. The alcohols mixture (6.8 kg) was obtained with a purity of 92.91%. The melting point of M.H.P.A.A. is 78.5°–80.5° C. Table 7 shows the qualitative and quantitative composition of M.H.P.A.A. obtained by this procedure.

TABLE 7

| Qualitative and quantitative composition of M.H.P.A.A. obtained. | |
|---|---|
| Component | Percentage of each alcohol |
| 1 - tetracosanol | 0.75 |
| 1 - hexacosanol | 7.00 |
| 1 - heptacosanol | 3.14 |
| 1 - octacosanol | 63.60 |
| 1 - nonacosanol | 0.62 |
| 1 - triacontanol | 12.03 |
| 1 - dotriacontanol | 4.99 |
| 1 - tetratriacontanol | 0.78 |

EXAMPLE 5

Twenty (20) kg of refined sugar cane wax previously melted at a temperature of 100°–110° C., are taken, adding 3.7 kg of potassium hydroxide diluted in 3.0 L of water. The saponification process lasted 5 hours performed with continuous stirring. The extraction of M.H.P.A.A. is performed with a Soxhlet extractor using methyl ethyl ketone as solvent for 14 hours. The extracted material is cooled at room temperature. Further on, it is recrystallized into a mixture of hexane:chloroform 1:1. M.H.P.A.A. (3.8 kg) was obtained with a purity accounting for a 92.56%. The melting point of M.H.P.A.A. ranges between 78.5° and 80.5° C. Table 8 shows the qualitative and quantitative composition of M.H.P.A.A. obtained using this procedure.

TABLE 8

| Qualitative and quantitative composition of M.H.P.A.A. obtained | |
|---|---|
| Component | Percentage of each alcohol |
| 1 - tetracosanol | 0.85 |

TABLE 8-continued

| Qualitative and quantitative composition of M.H.P.A.A. obtained | |
|---|---|
| Component | Percentage of each alcohol |
| 1 - hexacosanol | 6.56 |
| 1 - heptacosanol | 3.10 |
| 1 - octacosanol | 63.10 |
| 1 - nonacosanol | 0.72 |
| 1 - triacontanol | 12.18 |
| 1 - dotriacontanol | 5.31 |
| 1 - tetratriacontanol | 0.74 |

EXAMPLE 6

One kg of raw sugar cane wax melted previously at 100° C., adding 250 g of calcium hydroxide. The saponification process is done with continuous stirring for 2 h. M.H.P.A.A. is extracted using 2-propanol as solvent for 12 h in a solid-liquid extraction system. The product obtained is cooled at room temperature, whereby is re-crystallized using heptane. M.H.P.A.A. (165 g) was obtained with a purity of 93.63%. The melting point of this M.H.P.A.A. ranges from 80.0°–81.5° C. Table 9 shows the qualitative and quantitative composition of M.H.P.A.A. obtained using this procedure.

TABLE 9

| Qualitative and quantitative composition of M.H.P.A.A. obtained | |
|---|---|
| Component | Percentage of each alcohol |
| 1 - tetracosanol | 0.84 |
| 1 - hexacosanol | 6.52 |
| 1 - heptacosanol | 3.18 |
| 1 - octacosanol | 64.13 |
| 1 - nonacosanol | 0.69 |
| 1 - triacontanol | 12.54 |
| 1 - dotriacontanol | 4.93 |
| 1 - tetratriacontanol | 0.80 |

EXAMPLE 7

Two (2) kg of refined sugar cane wax melted previously at 110° C., adding 400 g of sodium hydroxide diluted in 200 mL of water. This process is mantained for 3 hours with continuous stirring. The extraction of M.H.P.A.A. is performed using toluene as solvent in a solid extractor for 6 hours, whereby it was secondly recrystallized using methanol as solvent. M.H.P.A.A. (389 g) was obtained with a purity accounting 95.10%. The melting point of the mixture ranges between 81.0° and 83.0° C. Table 10 shows the qualitative and quantitative composition of M.H.P.A.A. obtained using this procedure.

TABLE 10

| Qualitative and quantitative composition of M.H.P.A.A. obtained | |
|---|---|
| Component | Percentage of each alcohol |
| 1 - tetracosanol | 0.80 |

TABLE 10-continued

Qualitative and quantitative composition of M.H.P.A.A. obtained

| Component | Percentage of each alcohol |
|---|---|
| 1 - hexacosanol | 7.00 |
| 1 - heptacosanol | 2.82 |
| 1 - octacosanol | 64.54 |
| 1 - nonacosanol | 0.72 |
| 1 - triacontanol | 13.02 |
| 1 - dotriacontanol | 5.31 |
| 1 - tetratriacontanol | 0.89 |

EXAMPLE 8

Five (5) kg of refined sugar cane wax were treated with 1 kg of potassium hydroxide diluted in 500 mL of water afyter melting it at 120° C. This process is mantained for 4 hours with continuous stirring. M.H.P.A.A. is extracted using ethanol as solvent, in a solid-liquid extraction system during 5 h. After that, the extract is cooled at room temperature. Whereby, M.H.P.A.A. is crystallized using toluene as solvent. M.H.P.A.A. (1490 g) was obtained with a purity accounting for a 92.20%. The melting point of M.H.P.A.A. ranges between 79.5° and 81.0° C. Table 11 shows the qualitative and quantitative composition of M.H.P.A.A. obtained using this procedure.

TABLE 11

Qualitative and quantitative composition of M.H.P.A.A. obtained

| Component | Percentage of each alcohol |
|---|---|
| 1 - tetracosanol | 0.76 |
| 1 - hexacosanol | 6.58 |
| 1 - heptacosanol | 2.84 |
| 1 - octacosanol | 62.43 |
| 1 - nonacosanol | 0.71 |
| 1 - triacontanol | 13.60 |
| 1 - dotriacontanol | 5.05 |
| 1 - tetratriacontanol | 0.75 |

EXAMPLE 9

The compositions of two different developed pharmaceutical formulations, using this M.H.P.A.A. as active principle are shown in Table 12. These formulations were developed taking into account the physical, chemical and physicochemical characteristics of the active principle. The formulations were manufactured by a wet granulation process mixing the active principle and the pharmaceutical excipients with controlled portions, drying, degranulating, lubricating and stamping them.

TABLE 12

Pharmaceutical formulations using M.H.P.A.A as active principle

| Component | Formulation 1 (%) | Formulation2 (%) |
|---|---|---|
| M.H.P.A.A. | 5.0 | 15.0 |
| Lactose | 56.0 | 54.0 |
| Corn Starch | 15.0 | 10.0 |

TABLE 12-continued

Pharmaceutical formulations using M.H.P.A.A as active principle

| Component | Formulation 1 (%) | Formulation2 (%) |
|---|---|---|
| Gelatin | 2.5 | 2.0 |
| Sodium croscarmellose | 5.0 | 4.0 |
| Saccharose | 5.0 | 4.0 |
| Talc | 2.0 | 2.0 |
| Magnesium stearate | 1.5 | 1.0 |
| Cellulose acetophtalate | 0.5 | 1.0 |
| Microcrystalline cellulose | 7.5 | 7.0 |

EXAMPLE 10

Male New Zealand rabbits (2–3 kg) were adapted to laboratory conditions for 15 days and randomly distributed in 4 experimental groups: a control (only receiving vehicle) and 3 M.H.P.A.A. treated groups at 5, 50 and 200 mg/kg receiving M.H.P.A.A. suspended in an Acacia gum/water vehicle by gastric gavage (1 mL/kg) for 4 weeks. Lipid profile was determined at baseline (the day before starting the treatment and 4 weeks after). M.H.P.A.A. administered orally at 5, 50 and 200 mg/kg during 30 days significantly reduced (Wilcoxon $p<0.05$) in a dose-dependent manner total cholesterol and LDL-serum levels. Moreover, the percent changes in control and treated groups were statistically different (Mann Whitney U, $p<0.05$), see FIGS. 1–4.

Figure 2:
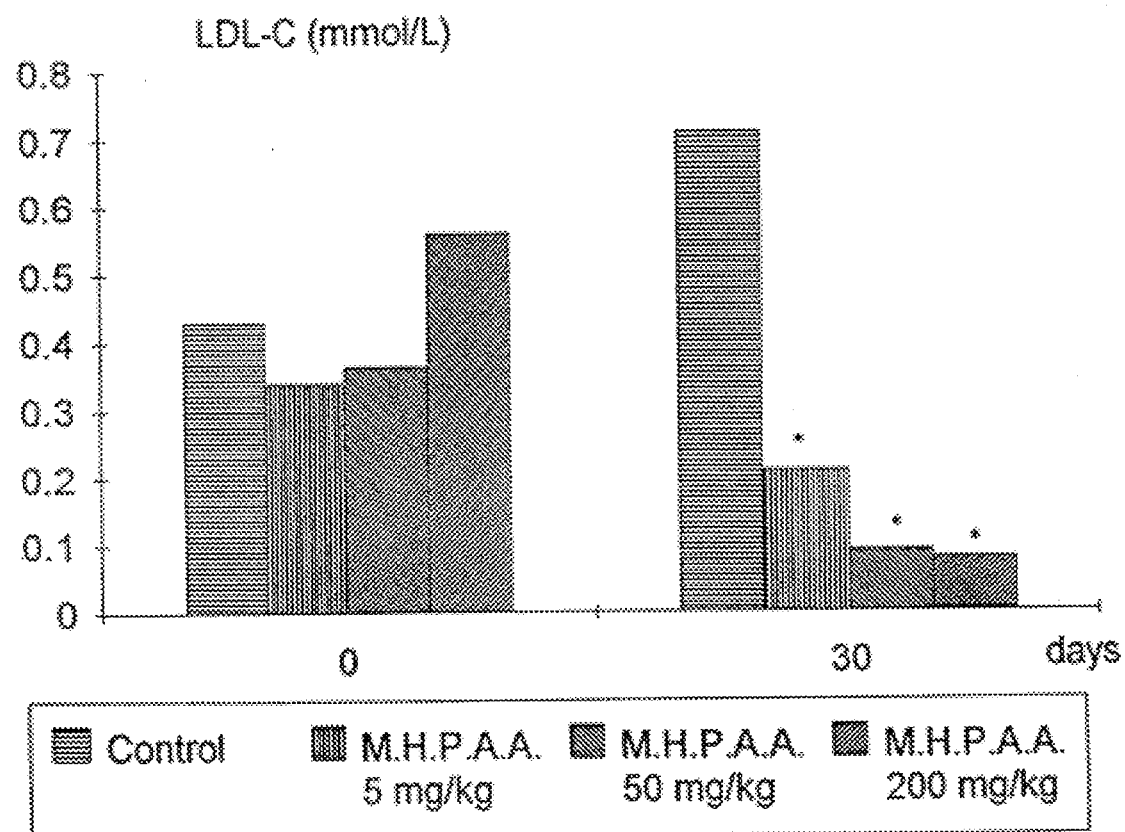
Figure 3:
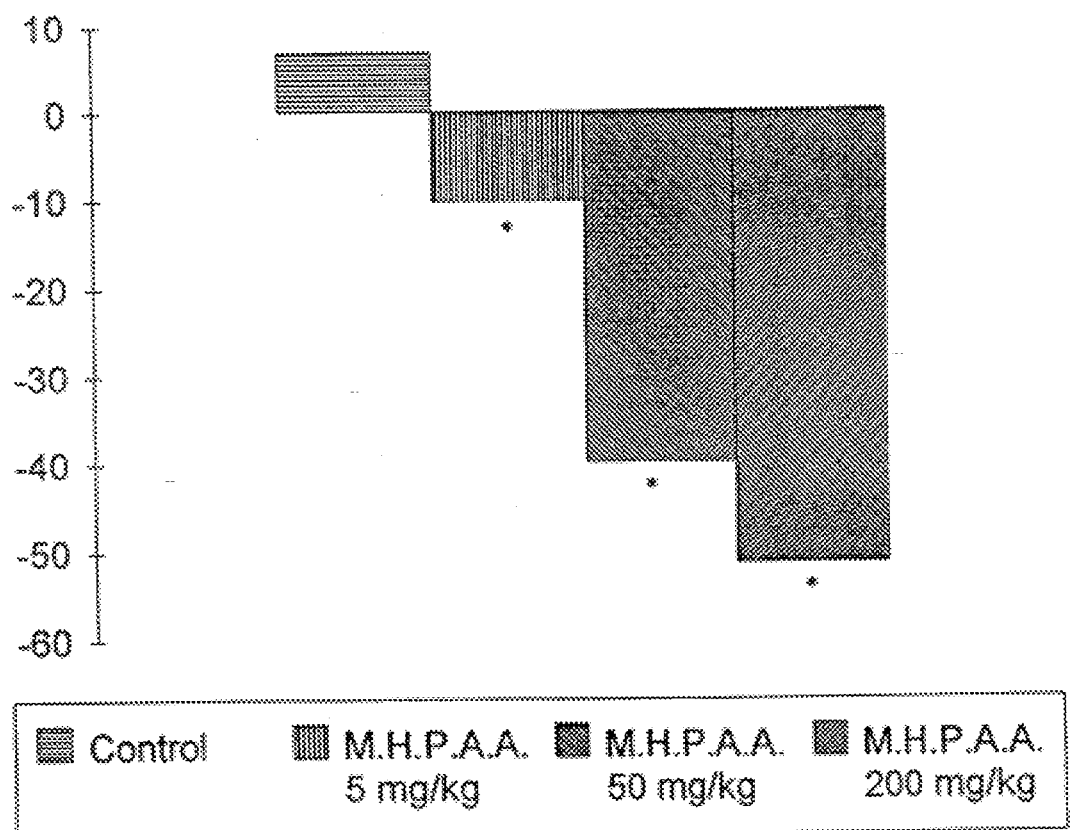
Figure 4:
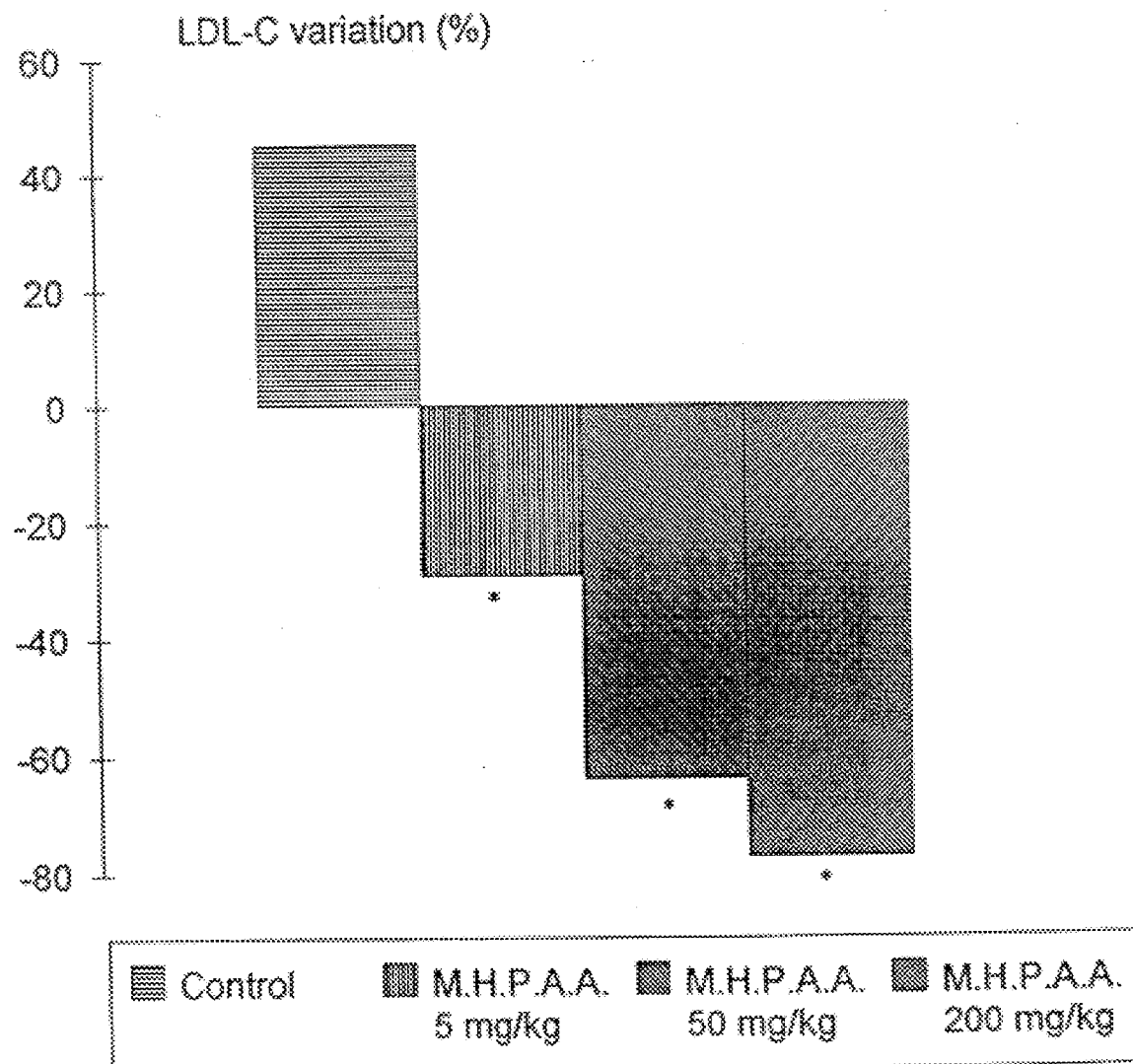

FIG. 1 shows the effect of M.H.P.A.A. on serum cholesterol levels, FIG. 2 on serum LDL-C levels, FIG. 3 on serum cholesterol changes and FIG. 4 on serum LDL-C changes (%) in normocholesterolemic rabbits.

Figure 5:
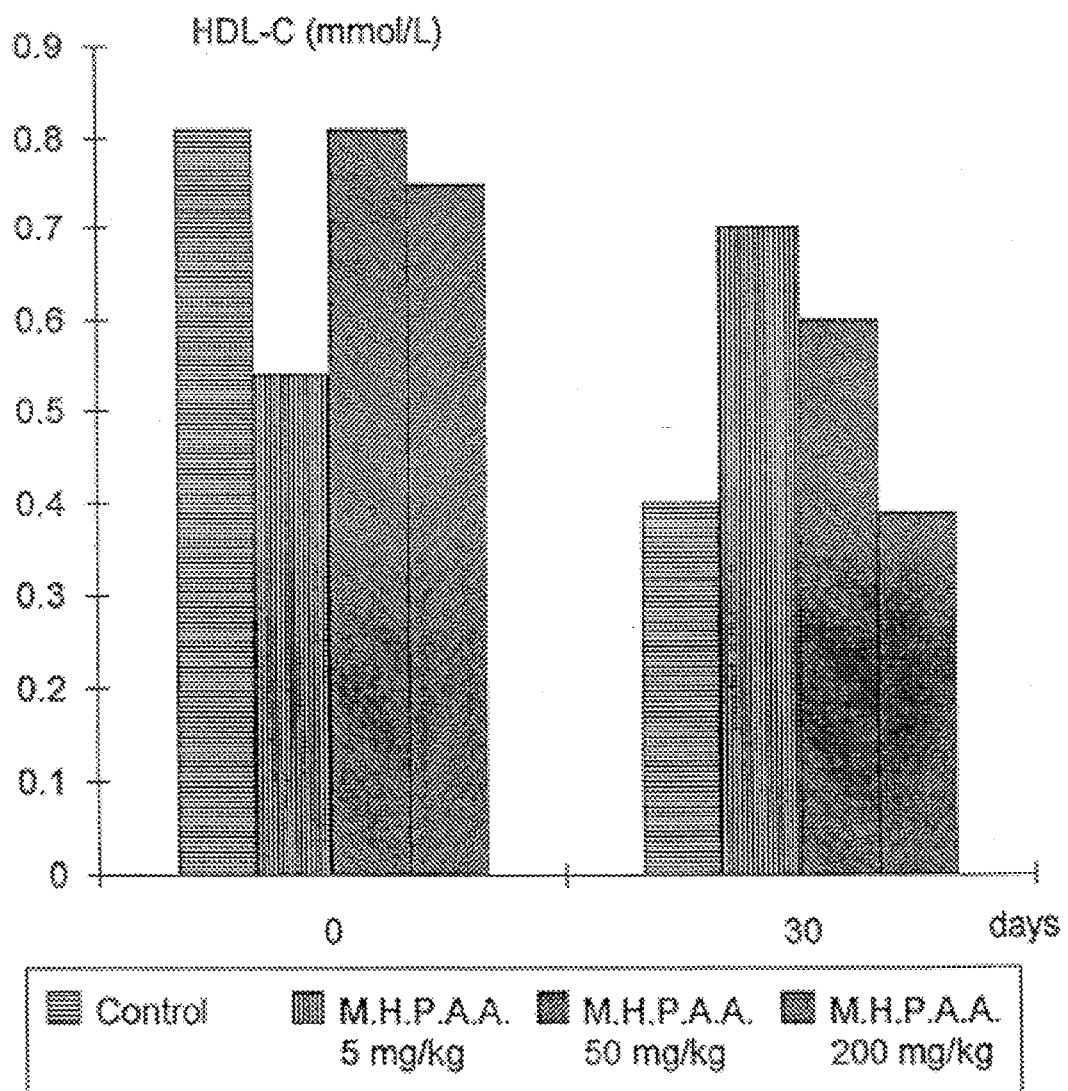

In this experimental series, the highest dose of M.H.P.A.A. administered (200 mg/kg) reduced serum cholesterol and LDL-C by 51 and 78%, respectively. FIG. 5 shows the effect of M.H.P.A.A. in normocholesterolemic rabbits. No significant changes in HDL-C levels were produced in all four groups.

Figure 6:
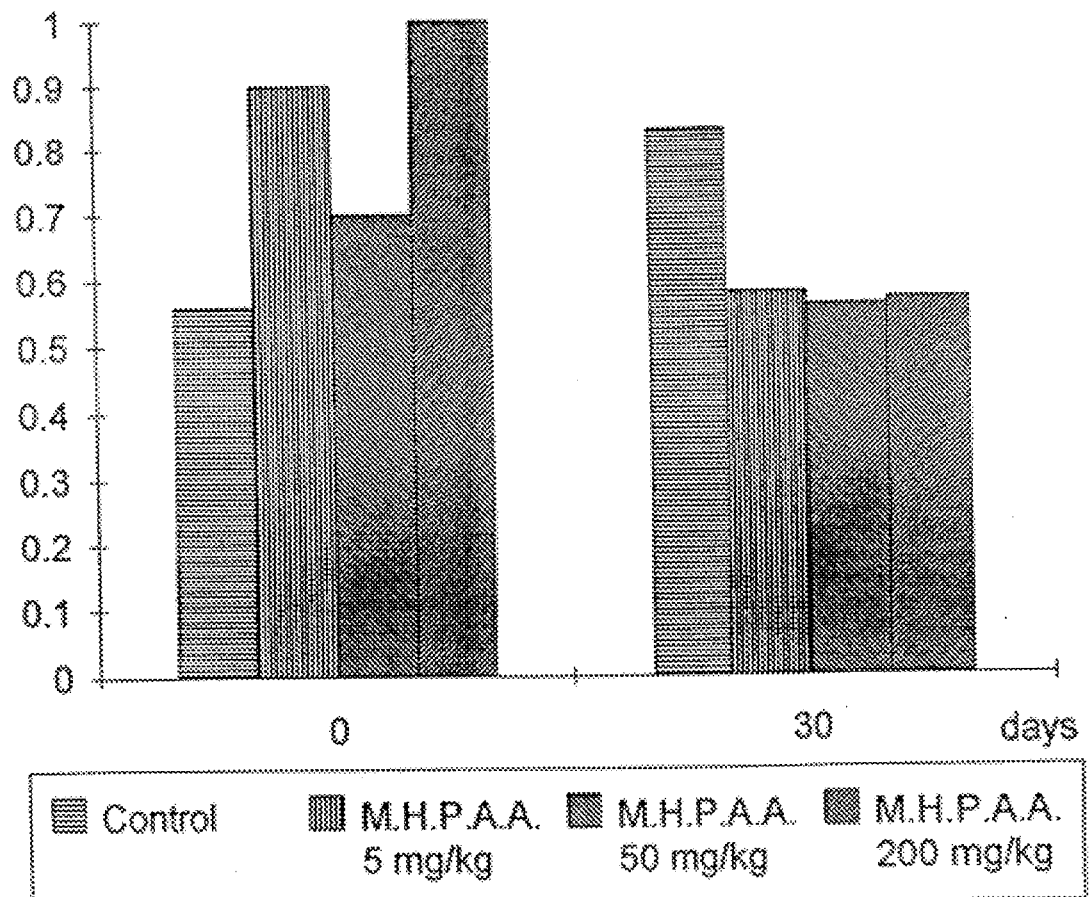
Figure 7:
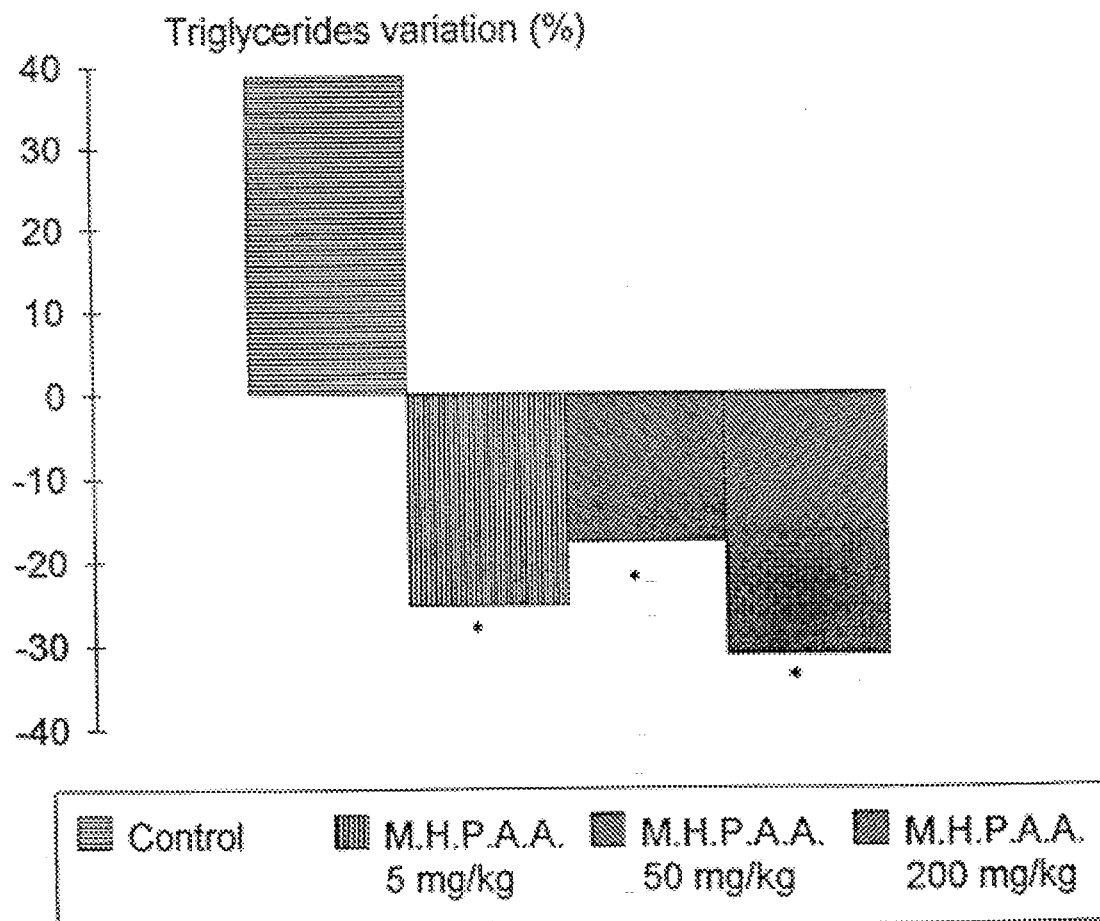

FIG. 6 illustrates the effect of M.H.P.A.A. on serum triglycerides and FIG. 7 on serum tryglicerides changes in normocholesterolemic rabbits. Comparison of triglycerides percent changes between treated and control groups were also significant (Mann Whitney U, $p<0.05$), but no dose-effect relationship was observed.

EXAMPLE 11

Male New Zealand rabbits were distributed randomly in 4 groups: a control group (only receiving vehicle by gastric gavage) and 3 groups treated M.H.P.A.A., octacosanol and hexacosanol, respectively at 5 mg/kg. Serum lipid profile was determined at baseline and 30 days before treatment. M.H.P.A.A. decreased significantly total cholesterol and LDL-C. Moreover, levels of cholesterol, LDL-C and triglycerides of M.H.P.A.A.-treated rabbits were significantly lower than those of the controls. Nevertheless, the changes on serum lipid profile occurred in groups treated with octacosanol or hexacosanol did not achieve statistical significance as is shown in Table 13.

TABLE 13

Effects of M.H.P.A.A., octaconsanol and hexacosanol on serum lipid profile (mmol/L) of New Zealand normocholesterolemic rabbits (mean values)

| Group | Dose (mg/kg) | Baseline | After treatment |
|---|---|---|---|
| Total cholesterol | | | |
| Controls | 0 | 2.5 | 2.3 |
| M.H.P.A.A. | 5 | 2.8 | 1.6 *+ |
| Octacosanol | 5 | 2.7 | 2.2 |
| Hexacosanol | 5 | 2.6 | 2.4 |
| LDL-C | | | |
| Control | 0 | 1.5 | 1.2 |
| M.H.P.A.A. | 5 | 1.3 | 0.6 *+ |
| Octacosanol | 5 | 1.4 | 0.9 |
| Hexacosanol | 5 | 1.5 | 1.0 |
| Triglycerides | | | |
| Control | 0 | 0.80 | 0.82 |
| M.H.P.A.A. | 5 | 0.78 | 0.55 * |
| Octacosanol | 5 | 0.77 | 0.70 |
| Hexacosanol | 5 | 0.80 | 0.78 |

* $p < 0.05$ comparison with controls (Mann Whitney U test)
+ $p < 0.05$ comparison with baseline (Wilcoxon)

EXAMPLE 12

After 5 weeks of diet-only period, forty five outpatients whom cholesterol and LDL-C values were not enough controlled by diet received tablets containing 5 mg of M.H.P.A.A. (twice-a-day at lunch and dinner) or placebo for 6 weeks. During this active treatment period, dietary conditions were mantained. Lipid profile levels were determined at baseline (end of the diet-only period) as well as 4 and 6 weeks after therapy. M.H.P.A.A. reduced significantly total serum cholesterol by 16.23% and LDL-C by 21.33%. Also cholesterol to HDL-C and LDL-C to HDL-C ratios were significantly reduced to 17.67% and 22.28%, respectively ($p<0.05$ Wilcoxon test for paired data). In all patients levels of both total cholesterol and LDL-C were lower 6 weeks after treatment that at baseline. Changes on other lipid profile fractions were non significant, results are shown in Tables 14 and 15.

TABLE 14

Effects of M.H.P.A.A. (10 mg/day, 5 mg twice-a-day) on serum lipid profile (mmol/L) in patients with Type II hyperliproteinemia

| | n | Baseline (X + SD) | week 6 (X + SD) |
|---|---|---|---|
| Total cholesterol | | | |
| M.H.P.A.A. | 22 | 7.43 + 1.29 | 6.21 + 1.38 *** "" |
| placebo | 23 | 6.97 + 0.72 | 6.70 + 0.75 * |
| LDL-C | | | |
| M.H.P.A.A. | 22 | 5.54 + 1.22 | 4.35 + 1.31 *** """ a |
| placebo | 23 | 5.07 + 0.63 | 4.97 + 0.67 |
| HDL-C | | | |
| M.H.P.A.A. | 22 | 1.03 + 0.26 | 1.10 + 0.28 |
| placebo | 23 | 1.13 + 0.31 | 1.02 + 0.28 |
| Triglycerides | | | |
| M.H.P.A.A. | 22 | 2.41 + 0.94 | 1.74 + 0.88 |
| placebo | 23 | 2.03 + 0.64 | 1.87 + 0.67 |
| VLDL-C | | | |
| M.H.P.A.A. | 22 | 1.09 + 0.43 | 0.79 + 0.40 |
| placebo | 23 | 0.92 + 0.29 | 0.85 + 0.31 |

TABLE 14-continued

Effects of M.H.P.A.A. (10 mg/day, 5 mg twice-a-day) on serum lipid profile (mmol/L) in patients with Type II hyperliproteinemia

| | n | Baseline (X + SD) | week 6 (X + SD) |
|---|---|---|---| n number of patients
* $p < 0.01$; *** $p < 0.0001$ comparison with baseline (Wilcoxon)
a $p < 0.05$ comparison with placebo, absolute values, Mann Whitney U test
"" $p < 0.0001$ comparison with placebo (Mann Whitney U test)
""" $p < 0.00001$ comparison with placebo (Mann Whitney U test)

TABLE 15

Effects of M.H.P.A.A. (10 mg/day, 5 mg twice-a-day) on serum lipid ratios (mmol/L) in patients with Type II hyperliproteinemia

| | n | Baseline (X + SD) | week 6 (X + SD) |
|---|---|---|---|
| LDL-C to HDL-C | | | |
| M.H.P.A.A. | 22 | 5.71 + 1.82 | 4.18 + 1.59 ** ""a |
| placebo | 23 | 4.92 + 1.85 | 5.30 + 1.79 |
| Cholesterol to HDL-C | | | |
| M.H.P.A.A. | 22 | 7.65 + 2.18 | 5.94 + 1.81 * " |
| placebo | 23 | 6.69 + 2.21 | 7.06 + 2.05 |

* $p < 0.05$; ** $p < 0.01$ comparison with baseline (Wilcoxon)
a $p < 0.05$ comparison with placebo, absolute values, Mann Whitney U test
" $p < 0.05$ comparison with placebo (Mann Whitney U test)
"" $p < 0.01$ comparison with placebo (Mann Whitney U test)

EXAMPLE 13

A group of patients with Type II hyperlipoproteinemia received tablets containing 15 mg of the formulation after 8 weeks of diet-only period (baseline). Lipid profile was determined at baseline and 8 weeks after therapy. The main results are summarized in Table 16. Formulation with M.H.P.A.A. significantly reduced serum total cholesterol by 16.44% and LDL-C by 23.51%.

Figure 8:
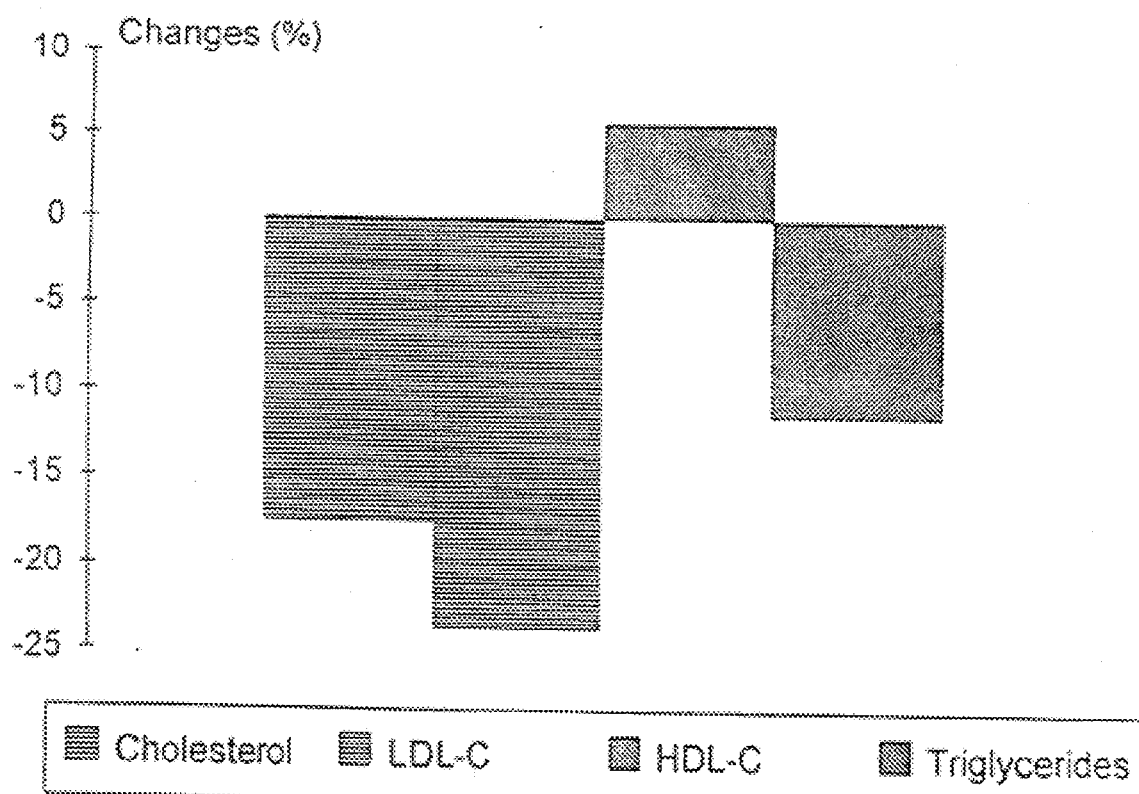

FIG. 8 shows the effect of M.H.P.A.A. on the lipid profile of patients with Type II hyperlypoproteinaemia, whereby the changes of cholesterol, LDL-C and HDL-C are indicated mean values and the change of triglycerides as median value. HDL-C raised 6.40%, while triglycerides and VLDL-C decreased 7.80% and 10.83%, respectively but these changes were not statistically significant. In Table 17 are shown the changes on the LDL-C to HDL-C and cholesterol to HDL-C ratios, they were decreased significantly by 29.07% and 23.72%, respectively.

TABLE 16

Effects of M.H.P.A.A. on serum lipids profile and lipoproteins in patients with Type II hyperliproteinemia

| Parameters | n | Baseline (X + SD) | n | 8 weeks (X + SD) |
|---|---|---|---|---|
| Cholesterol | 25 | 7.84 + 1.14 | 25 | 6.50 + 1.21 **** |
| LDL-C | 17 | 5.86 + 1.11 | 18 | 4.33 + 1.32 ** |
| HDL-C | 19 | 1.03 + 0.44 | 20 | 1.21 + 0.46 |
| Triglycerides | 19 | 2.30 + 1.42 | 20 | 2.14 + 1.06 |
| VLDL-C | 19 | 1.05 + 0.64 | 20 | 0.97 + 0.48 |

TABLE 16-continued

Effects of M.H.P.A.A. on serum lipids profile
and lipoproteins in patients with Type II
hyperliproteinemia

| Parameters | n | Baseline (X + SD) | n | 8 weeks (X + SD) |
|---|---|---|---|---| p < 0.01; ** p < 0.0001 (Wilcoxon test)

TABLE 17

Effects of M.H.P.A.A. on LDL-C ato HDL-C and
cholesterol to HDL-C ratios in patients with Type
II hyperliproteinemia

| Parameters | n | Baseline (X + SD) | n | 8 weeks (X + SD) |
|---|---|---|---|---|
| LDL-C to HDl-C | 17 | 6.34 + 2.79 | 18 | 3.82 + 1.55 ** |
| Cholesterol to HDL-C | 19 | 8.83 + 3.49 | 20 | 6.07 + 2.17 ** |

** p < 0.01 (Wilcoxon test)

EXAMPLE 14

Firstly, it was investigated the effect of M.H.P.A.A. and its effect on ADP and collagen-induced platelet aggregation in rats. A group of male Sprague-Dawley rats weighing 250 to 350 g were distributed randomly between 2 experimental groups. M.H.P.A.A. was administered orally as a suspension in a Acacia gum-water vehicle by gastric gavage for 4 weeks. The following groups were included: Control group (only receiving vehicle) and a M.H.P.A.A. (25 mg/kg) treated group. To conduct the platelet aggregation assay, rats were anaesthetized in an ether atmosphere. Abdomens were opened and blood (5 mL) was drawn from the vena cava and mixed with 3.8% sodium citrate (1 volume of citrate per 9 of blood). Platelet-rich plasma (PRP) was obtained by blood centrifugation. Platelet-poor plasma (PPP) was obtained by PRP aliquot centrifugation 330xg for 15 minutes. Platelet aggregation was induced by ADP and by collagen and measured with a Payton aggregometer as described (McGregor L., Morazain R. and Renaud S.; 1980; Effect of dietary linoleic acid on platelet functions in the rat; Thrombosis Res. 20, 499). The statistical comparison of results between treatment and control groups was carried out using the non parametric Mann-Whitney U Test. Rats treated with M.H.P.A.A. at 25 mg/kg for 4 weeks showed a significant inhibition of platelet aggregation ex vivo when submaximum ADP and collagen doses were administered.

Figure 9:
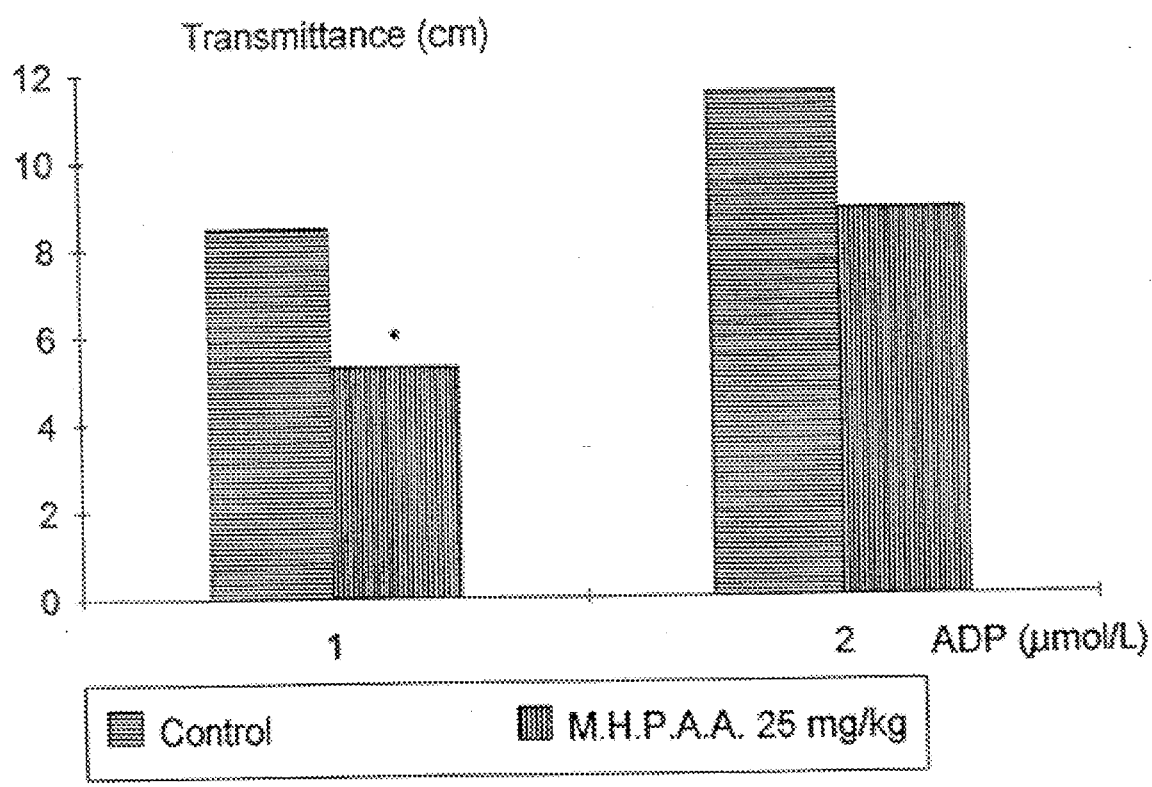
Figure 10:
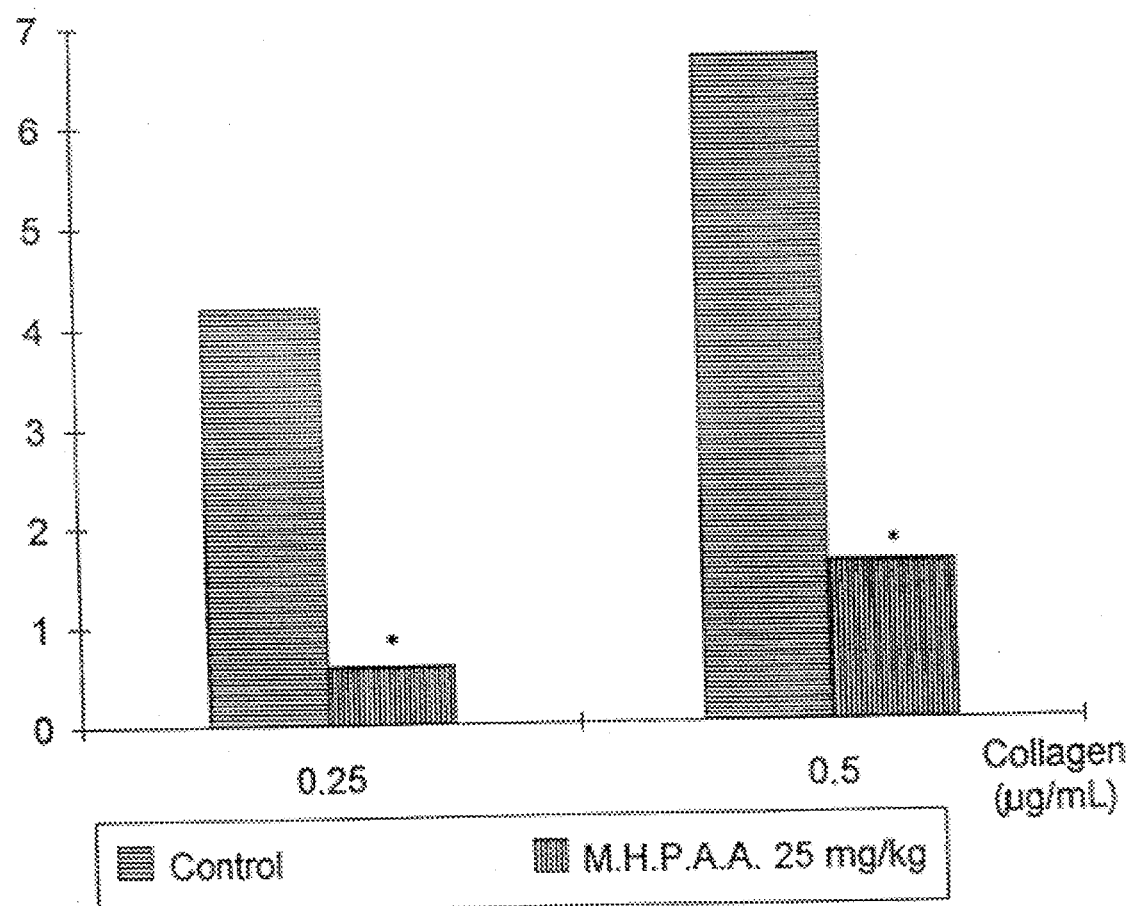

FIGS. 9 shows ADP-induced platelet aggregation in rats administered with M.H.P.A.A. for 1 month and FIG. 10 the collagen induced platelet aggregation in rats administered with M.H.P.A.A. for 1 month (p<<0.05, Mann-Whitney U test, 15 cm % transmittance). M.H.P.A.A. administered orally for 4 weeks to the rats inhibited significantly ADP and collagen-induced platelet aggregation suggesting that M.H.P.A.A. acts as an antiplatelet drug.

EXAMPLE 15

To characterize the effect of M.H.P.A.A. on ex vivo platelet aggregation in rats, some studies of the time course of its platelet antiaggregatory effects were done. For that purpose, Sprague-Dawley rats of both sexes weighing 250 to 350 g were distributed in 4 experimental groups: one control group and 3 groups treated with single doses of M.H.P.A.A. at 25, 50 and 200 mg/kg, respectively. Moreover, after 2, 6 and 24 h of administering the 200 mg/kg dose, the effects on platelet agreggation were investigated.

M.H.P.A.A. was prepared as described in Example 14 and administered orally as single doses, two hours prior to the experiment. Control animals receiving the same volume of vehicle. All animals were deprived of food, but had free access to water for 20 h prior to the experiment. All animals were anaesthetized with ether and blood samples were drawn from vena cava and mixed with 3.8% sodium citrate (9 volumes of blood per 1 of anticoagulant). Blood was centrifuged at 250 g for 10 minutes to obtain platelet-rich plasma (PRP). Once PRP was isolated, the rest was centrifuged at 1300 g for 15 minutes to obtain platelet-poor plasma (PPP).

Figure 11:
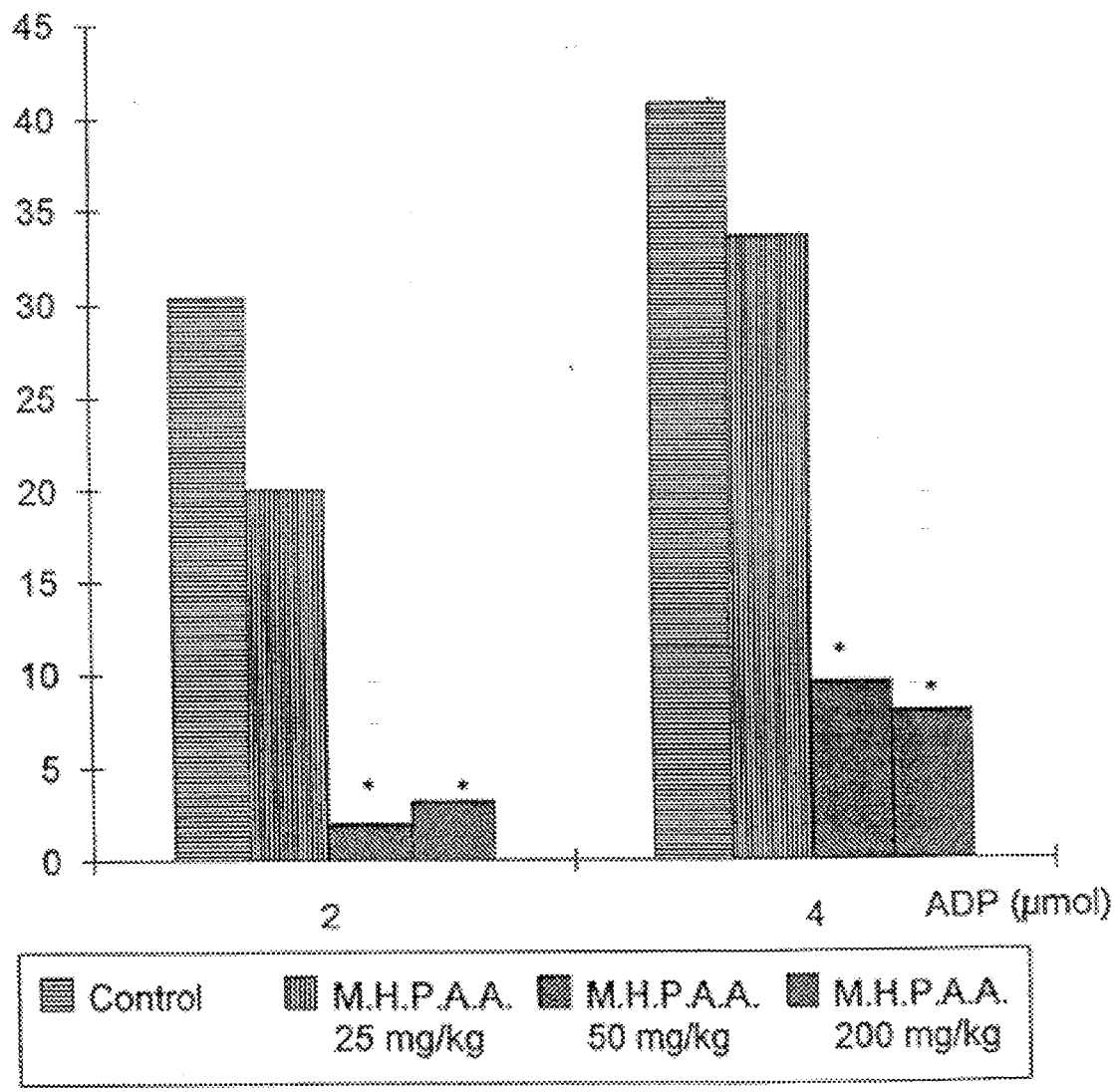

Platelet aggregation was quantified by turbidimetric method (Born G., 1962; Aggregation of blood platelets by adenosine diphosphate, and its reversal; Nature (London) 194, 927–929). Platelet aggregation levels were measured after calibrating the equipment at 0% of light transmission for PRP and at 100% for PPP. Aggregation curves were recorded for 5 min. FIG. 11 shows the effect of M.H.P.A.A. on ADP-induced platelet aggregation in rat platelet-rich plasma, p<<0.05 (Mann-Whitney U test). Results were expressed in percent of maximal aggregation(%). Groups were compared using the Mann-Whitney U test (p<<0.05).

M.H.P.A.A. (50 and 200 mg/kg) administered 2 h before blood sampling inhibited ADP-induced platelet aggregation, while lower doses (25 mg/kg) did not change significantly responses to ADP. The highest dose of M.H.P.A.A. (200 mg/kg) was chosen to study time course of anti-platelet effects.

Figure 12:
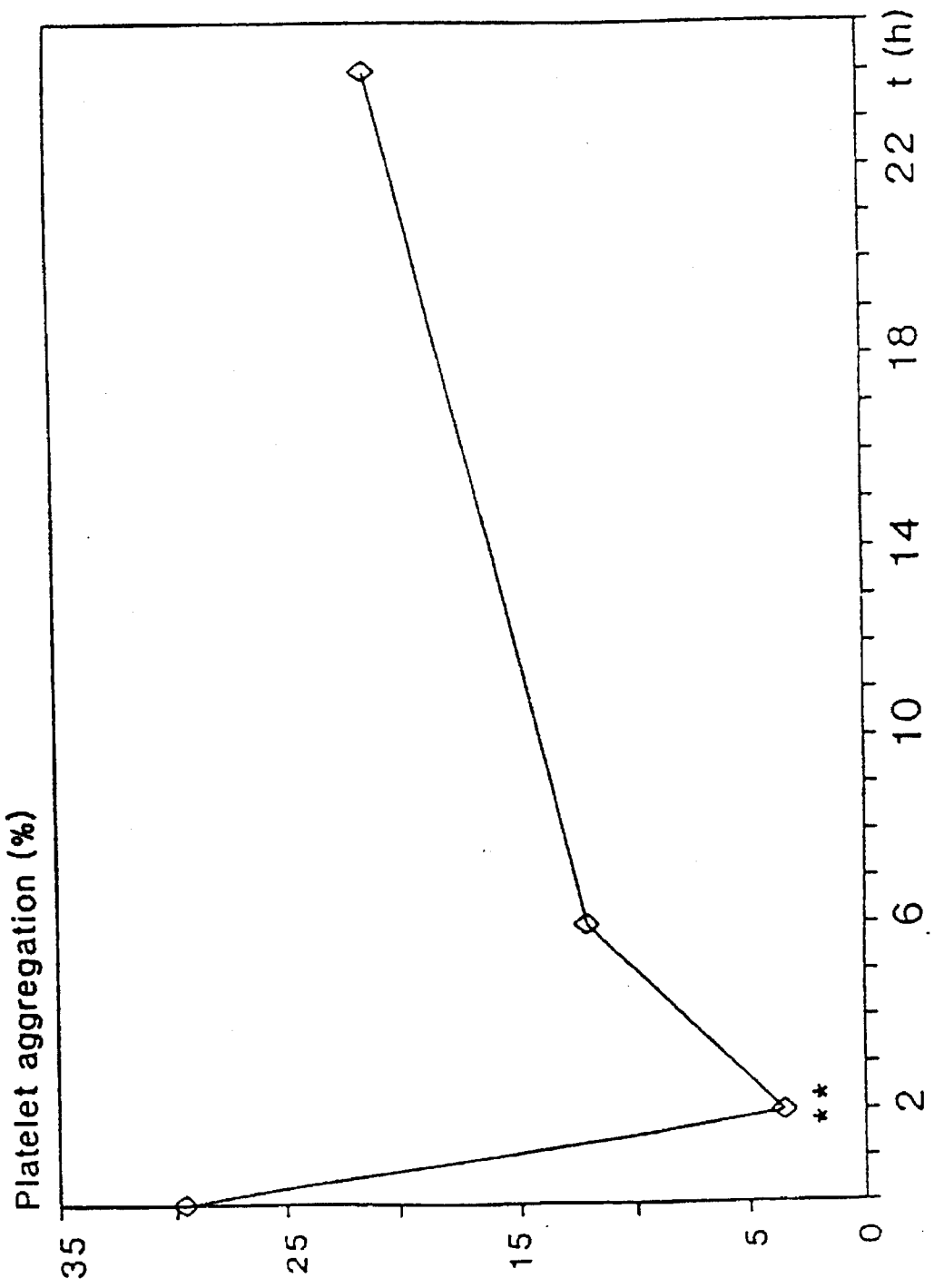

FIG. 12 shows the effect on ADP-induced platelet aggregation at a 2 µmol/L concentration, p<<0.01. Although after 2 h platelet aggregation was significantly inhibited, after 6 h the inhibition was only marginally significant (p=0.06), while 24 hours after no statistical significance was obtained. Results show that oral administration of policosanol to rats two h prior to blood sampling inhibited dose-dependently ADP-induced platelet agreggation in PRP of rats treated with M.H.P.A.A. at 50 and 200 mg/kg. The inhibitory effect of M.H.P.A.A. on ADP-induced aggregation is reversible, since 6 h after treatment with it at 200 mg/kg, inhibition of platelet aggregation was only marginally significant, and 24 h after treatment a lack of effectiveness was appreciated, showing that M.H.P.A.A. does not induce permanent cell modifications.

EXAMPLE 16

The effects of M.H.P.A.A. on "in vivo" intravascular platelet aggregation in rats and on collagen-induced mortality in mice were studied. Male Sprague Dawley rats weighing 250 to 300 g and 57BL6 female mice weighing 20 to 25 g were distributed randomly among different experimental groups. M.H.P.A.A. was prepared as described in Example 14, while. ASA was dissolved in 5% NaHCO$_3$. Drugs were administered orally by gavage 2 h before the assay. Animals received no food for 16 h prior to oral administration of the drugs. Rats were given 1 mL/100 g body weight and mice 0.5 mL/20 g body weight, control animals received equivalent volumes of the vehicle. Four experimental groups were used in the study of the intravascular platelet aggregation in rats: 1) Controls, 2, 3 and 4 M.H.P.A.A. at 5, 10 and 20 mg/kg. Animals were anaesthetized i.p. with pentobarbital sodium (30–40 mg/kg). A cannula was inserted into a carotid artery for blood sampling before and 90 seconds after a 30 mg/kg collagen i.v. injection into the penile vein.

Blood (900 μL) was collected in plastic tubes containing a 100 μL mixture with 0.7 mg/mL indomethacin and 19 mg/mL EDTA. An aliquote was used to determine platelet concentration in each sample through optic microscopic counting. Blood was then centrifuged and plasma malondialdehyde (MDA) concentration was quantified through the thiobarbituric acid method (Satoh M, 1978; Serum lipid peroxyde in cerebrovascular disorders determined by a new colorimetric method; Clin.Chim Acta 90,34–43). Platelet count and plasma MDA concentration variations after injecting collagen were expressed as a percent of baseline values. Differences between control and treatment groups were determined using the Mann-Whitney U Test.

For the study of the collagen induced mortality in rats, the experimental groups were the following: 1) controls: animals only receiving the vehicle, but inducing mortality by a collagen intravenous injection, 2) Animals pretreated with M.H.P.A.A. at 360 mg/kg 2 hours prior collagen injection; 3) Animals pretreated with M.H.P.A.A. at 360 mg/kg 1, 4, 8 and 24 hours prior to mortality induction and 4) Animals pretreated with M.H.P.A.A. at 180 mg/kg and ASA at 50 mg/kg 2 h prior to the assay.

Acid-soluble veal skin collagen type III was prepared as described (Kimura Y., Kaube T. and Watanabe K., 1985; Effect of celostagel on platelet aggregation and experimental thrombosis; Arzneim Forsch Drug Res. 35, 114–1148) and used at final concentration of 2.5 mg/mL. A 0.1 mL/20 g injection was administered via the retro-orbital plexus. This dose caused from 60 to 100% mortality in control animals. The comparison of the mortality percent between control and treatment animals was done using Fisher's Exact probability Test.

Figure 13:
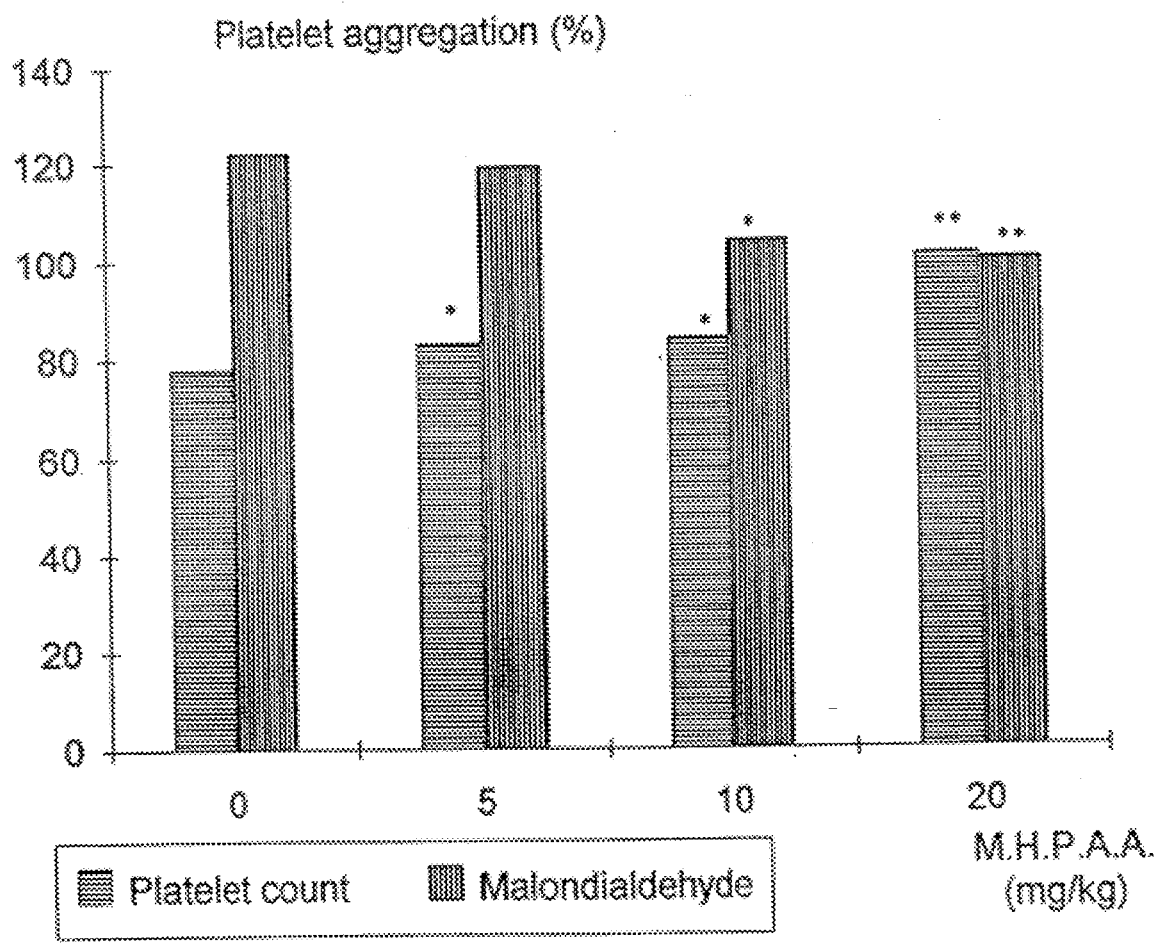

FIG. 13 shows the effect of M.H.P.A.A. on intravascular platelet aggregation in rats, $p<<0.05$; $p<<0.01$ (Mann Whitney U test). M.H.P.A.A. significantly inhibited the decrease in circulating platelet count and the simultaneous increase of MDA concentration in plasma induced by collagen.

Figure 14:
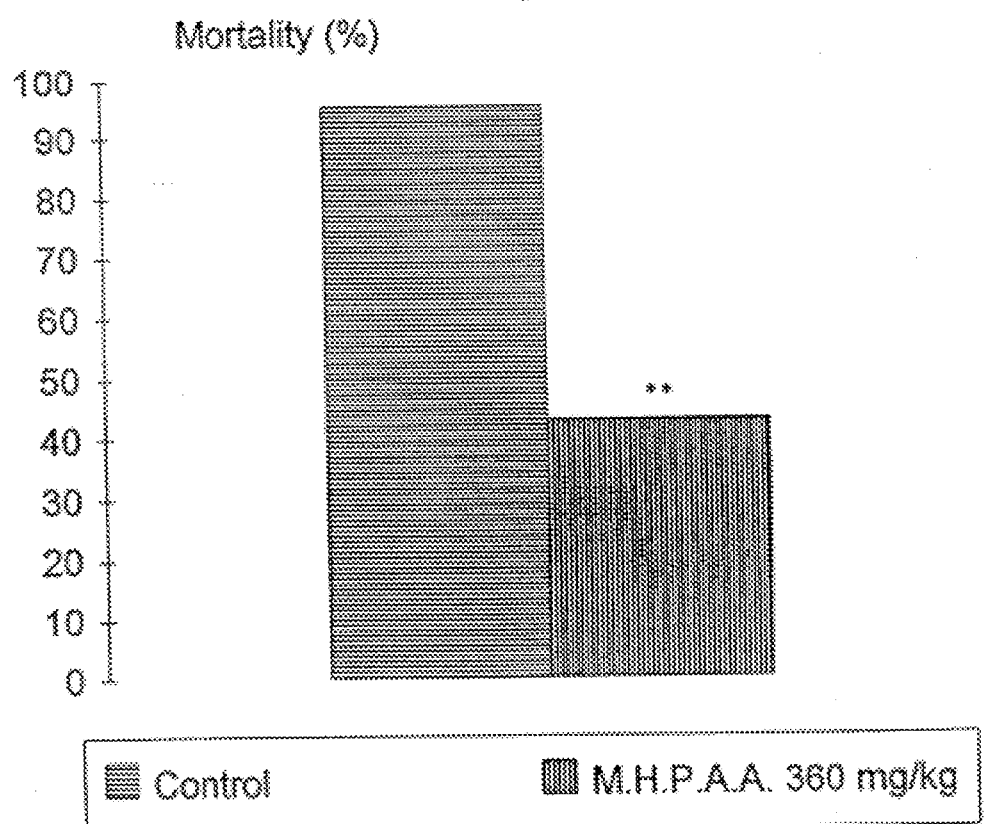
Figure 15:
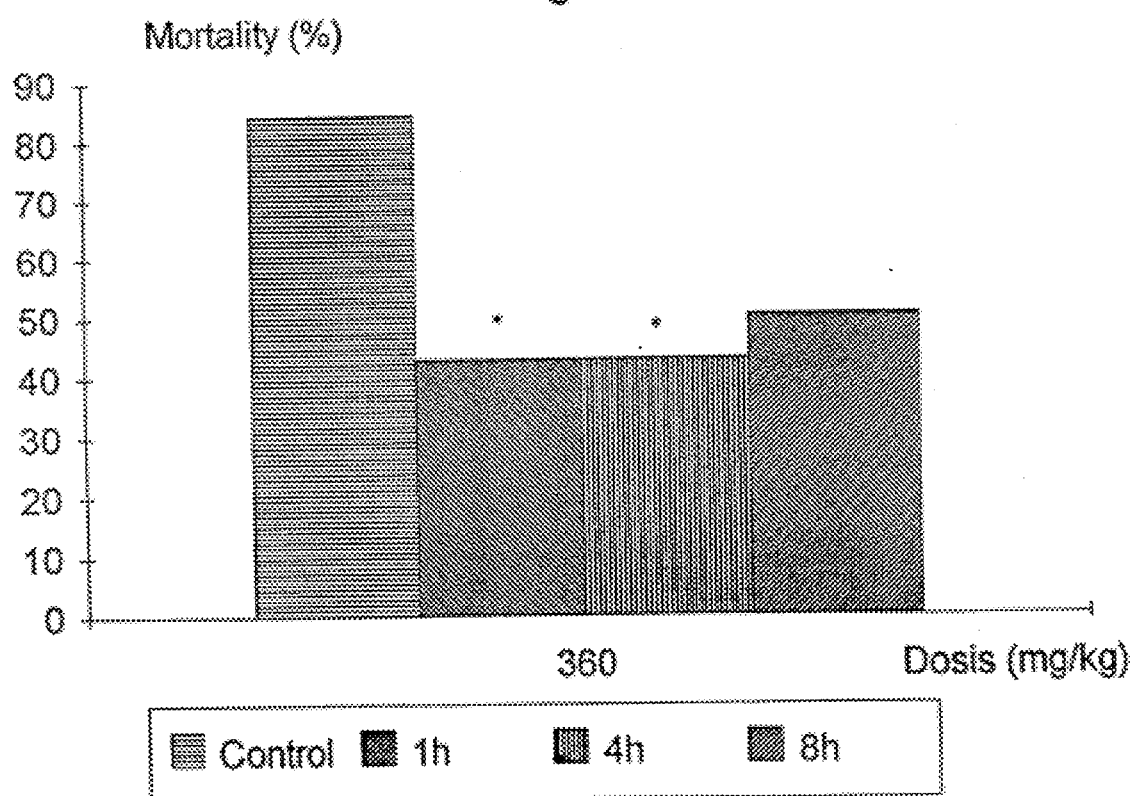

FIG. 14 demonstrates the effect of M.H.P.A.A. on collagen-induced mortality in C57BL6 mice, $p<<0.01$ (Mann-Whitney U test). Collagen-induced mortality was significantly reduced by M.H.P.A.A. at 360 mg/kg. This protective effect on the collagen induced mortality was observed when this dose was administered 1 and 4 hours prior to the assay, but significance was not obtained when administered 8 h before the assay. FIG. 15 shows the effect of M.H.P.A.A. on collagen-induced mortality in C57BL6 mice, $p<<0.05$ (Mann-Whitney U test).

Figure 16:
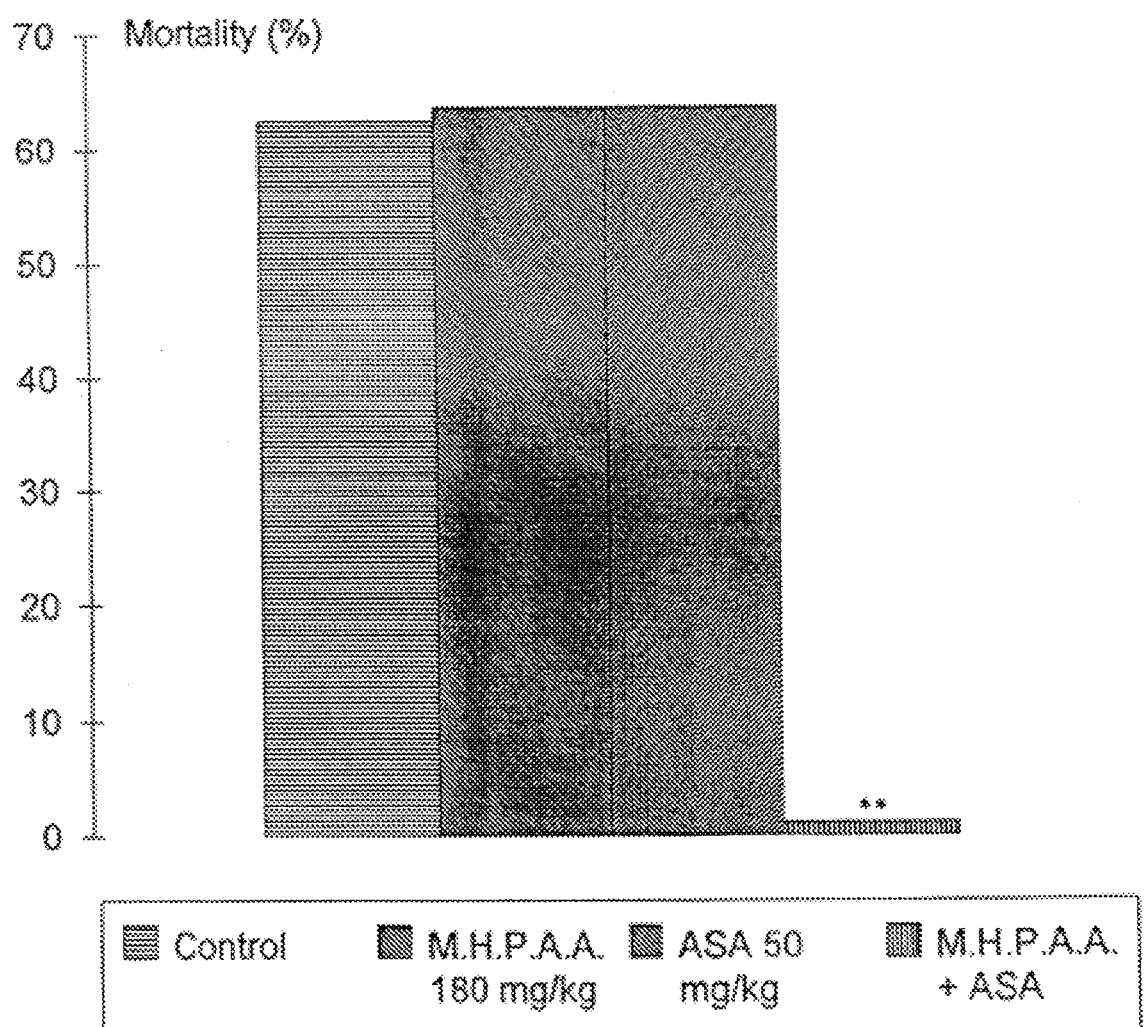

FIG. 16 illustrates the effect of combined administration of M.H.P.A.A. and ASA on collagen-induced mortality in mice, $p<<0.01$ (Fisher's exact probability Test). The combination of M.H.P.A.A. (180 mg/kg) and ASA (50 mg/kg) also caused a significant statistical decrease in collagen-induced mortality, while both treatments proved uneffective when administered independently.

Doses of M.H.P.A.A. and ASA that were uneffective when administered independently were obviously protective when administered together, thus indicating a synergism between M.H.P.A.A. and ASA antithrombotic effects.

EXAMPLE 17

For the analysis of M.H.P.A.A. effect on rat cerebral infarction, male Sprague Dawley rats weighing 290 to 330 g were distributed into the following experimental groups: 1) negative control: non-ligated rats receiving only the vehicle by gastric gavage, 2) positive control: ligated rats also receiving the vehicle by gastric gavage, 3) and 4) ligated rats receiving M.H.P.A.A. (5 and 25 mg/kg) by the same route. The different treatments were administered daily for 4 weeks. The last one was administered 12 h before ligation, as well as 8 and 24 h after the ligation, as commonly used in this model.

For the induction of cerebral ischemia, animals were gently anaestethized and oligemia was produced by bilateral ligation of the common carotid arteries. Immediately after, sodium nitroprusside (0.8 mg/250 g) was injected subcutaneously to induce arterial hypertension. Carotid clamps were removed 60 minutes after and animals were observed for 72 h and then sacrificed. Brains were rapidly removed and placed in an oven at 80° C. for 24 h. Both wet and dry weight were estimated to determine the water content (edema) and the following formula was applied:

$$\text{Edema} = \frac{\text{Wet weight} - \text{dry weight}}{\text{Wet weight}} \cdot 100$$

The statistical analysis of the results was carried out using the non-parametric Mann-Whitney U test. M.H.P.A.A. at 25 mg/kg decreased significantly the cerebral edema ($p<<0.05$) when is administered daily for 4 weeks. This dose also reduced mortality rates and percent of animals with edema, though these other reductions did not reach significant levels. These findings show that M.H.P.A.A. at 25 mg/kg significantly protect cerebral ischemia experimentally induced in rats, since a significant reduction in the brain edema was produced. There was also a reduction in the percent of animals treated showing brain edema areas, but this reduction did not reach significant levels (Table 18).

TABLE 18

Effect of M.H.P.A.A. on rat-induced brain ischemia

| Group | Doses (mg/kg) | Edema | Percent of Mortality | Animals |
|---|---|---|---|---|
| (−) Control | 0 | 79.3 +/− 0.39 | — | — |
| (+) Control | 0 | 80.1 +/− 0.82 | 35 | 54.5 |
| M.H.P.A.A. | 5 | 80.0 +/− 0.91 | 40 | 33.3 |
| M.H.P.A.A. | 25 | 79.5 +/− 0.49 * | 28 | 7.6 |

(−) controls: negative controls,
(+) controls: positive controls
* Significant differences compared with positive controls; $p << 0.05$ (Mann-Whitney U test)

EXAMPLE 18

To study the synergism between M.H.P.A.A. and aspirin on brain ischemia induced in rats, male Sprague Dawley rats weighing 250 to 300 g were distributed in 5 groups: 1) negative control (non ligated rats); 2) positive control (ligated animals receiving only the vehicle); 3) animals received orally by gavage 25 mg/kg of M.H.P.A.A.; 4) animals received orally ASA dissolved in 5% sodium bicarbonate 30 mg/kg; 5) rats administered orally ASA (30 mg/kg)+M.H.P.A.A. (25 mg/kg). Treatments were administered 2 hours prior the experiment.

Figure 17:
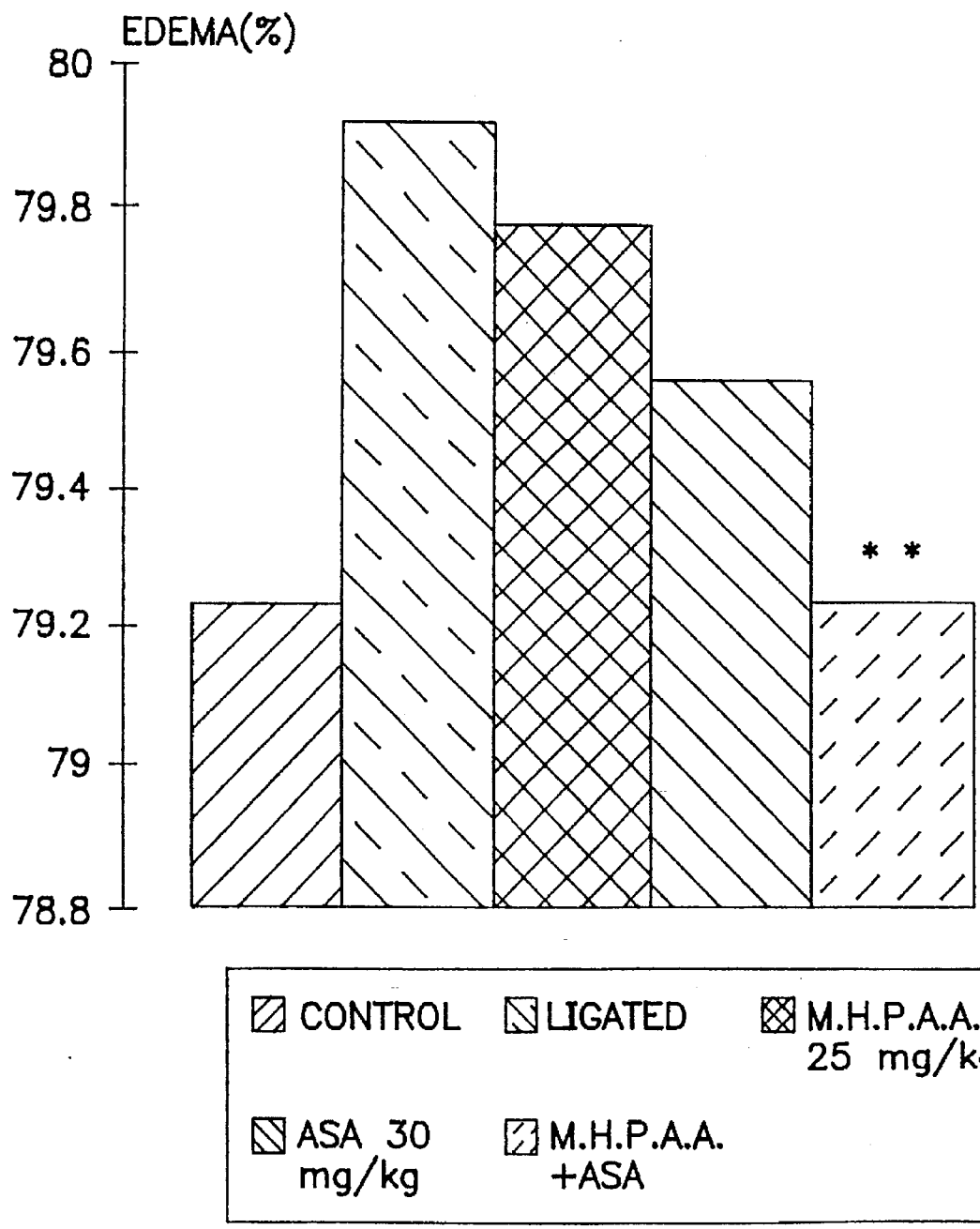

For the ischemia induction, animals were gently anaesthetized with wether and common arteries were dissected and ligated. Hypotension was then induced by a subcutaneous injection of sodium nitroprusside (0.8 mg/250 g). Carotid clamps were removed 60 min after and animals were observed for 24 hours. They were sacrificed and brains were removed immediately and placed in an oven at 80° C. for 24 h to determine water content. Results were analyzed using the non parametric Mann-Whitney U test. FIG. 17 shows the synergism between M.H.P.A.A. and ASA in cerebral ischemia in rats, p<<0.01 (Mann-Whitney U test). Neither M.H.P.A.A. nor aspirin reduced significantly brain ischemia when were separately administered to animals at the aforementioned doses. Nevertheless, when administered together a significant protection was obtained. These results confirm a synergism between anti-ischemic effects of M.H.P.A.A. and ASA.

EXAMPLE 19

Figure 18:
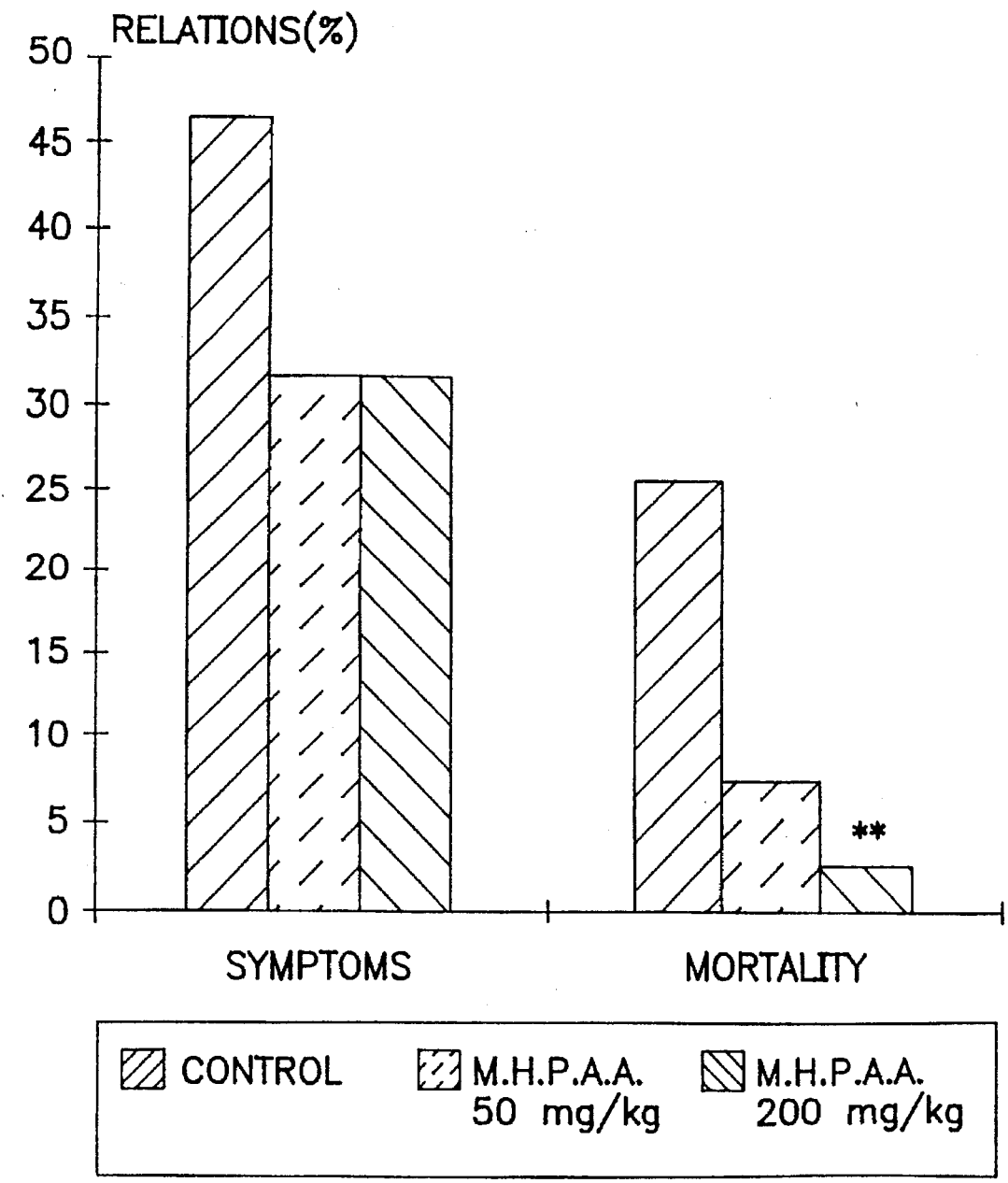

Mongolian gerbils of both sexes (60–80 g body weight) were used and adapted previously to laboratory conditions for a week. M.H.P.A.A. was administered by gastric gavage suspended in a Tween 20-water vehicle. Animals were distributed into the randomly following groups: (1) positive control (ligated animals, only receiving the vehicle), (2) M.H.P.A.A. (50 mg/kg) and (3) M.H.P.A.A. (300 mg/kg). All treatment were administered two hours prior induction of brain ischemia. The left common carotid artery was exposed in the neck and doubly ligated with surgical thread under ether anaesthesia. The behavior of each animal was observed for 24 h, recording the clinical symptoms of brain ischemia such as circling, rolling fits and seizures. Mortality was also recorded. Statistical comparison of the frequency of mortality and clinical symptons between groups were compared using the Fisher's Exact probability test. FIG. 18 shows the effect of M.H.P.A.A. on cerebral infarction induced in Mongolian gerbils, p<<0.05 (Mann-Whitney U test). Results show that treatment decrease symptoms and significantly reduced mortality.

It is well known that approximately 60% of Mongolian gerbils develop neurological deficits, such as circling behavior and rolling fits after ligation of common carotid artery. These symptoms have been associated with the fact that in approximately ⅔ of these animals there is an incompleteness or absence of connecting arteries between the basilar and carotid system. Moreover, almost a 80% of the animals showing clinical symptoms die within 72 h after ligation.

Since the severity of cerebral infarction of all brain regions is difficult to assess, while mortality rate is easy to quantify, this parameter have been used commonly for evaluate putative anti-ischemic drugs. Our results shows that M.H.P.A.A. (200 mg/kg) protects significantly the brain global ischemia induced by unilateral ligation of common artery in Mongolian gerbils. Thus, indicating usefulness of M.H.P.A.A. for prevent global ischemia development.

EXAMPLE 20

Effects of M.H.P.A.A. on gastric ulcer induced by different drugs were investigated. Sprague Dawley rats of both sexes, weighing 200 to 220 g were used. Animals were adapted to laboratory conditions for a week with water and food ad libitum. After a 24 h fast, rats were divided ramdomly into two experimental groups. The first group was intraperitoneally injected M.H.P.A.A. at 25 mg/kg suspended in a Tween 20/water vehicle, while the second group (control) only received the same volume of vehicle. In each case, experimental procedure for induction of different types of drug-induced gastric ulcer was performed in both control and treated groups (two groups were used for each type of ulcer):

A) Gastric ulcer experimentally induced by C4880 (Sigma). Procedure was simlar to that described by Awouters F., Nemegeens CJE and Jansken PAJ (1985: A pharmacological analysis of the rat mast cell 5-HT gastric lesion test and the effect of ketanserin; Drug. Div. Res. 5, 303–312).

For that, diphenhydramine was injected subcutaneously at 10 mg/kg and 30 min later C4880 was injected endovenously. Animals were sacrificed 4 h after C4880 administration and stomachs were removed quickly, opened lengthwise the greater curvature and washed with distilled water. Then, mucosas were exposed end damaged area was measured by means of a magnifying glass. Results were expressed as percent of area showing damage. In this model, pretreatments (M.H.P.A.A. or vehicle) were administered 30 min before diphenhydramine injection.

B) Ulcer induced by alcohol. Procedure was performed as described by Zengil H, Onik E, Erean TS and Tarker RK (1987: Protective effect of ilopnost and UK 38485 against gastric mucosal damage by various stimuli; Prostaglandins Leukotrienes and Medicine 30, 61–67). For that reason, one h after dosing M.H.P.A.A. or vehicle, rats were administered orally by gastric gavage ethanol 40% (1 mL/rat). Two hours later, rats were sacrificed and the procedure for quantifying gas gastric ulcer was performed as described.

Figure 19:
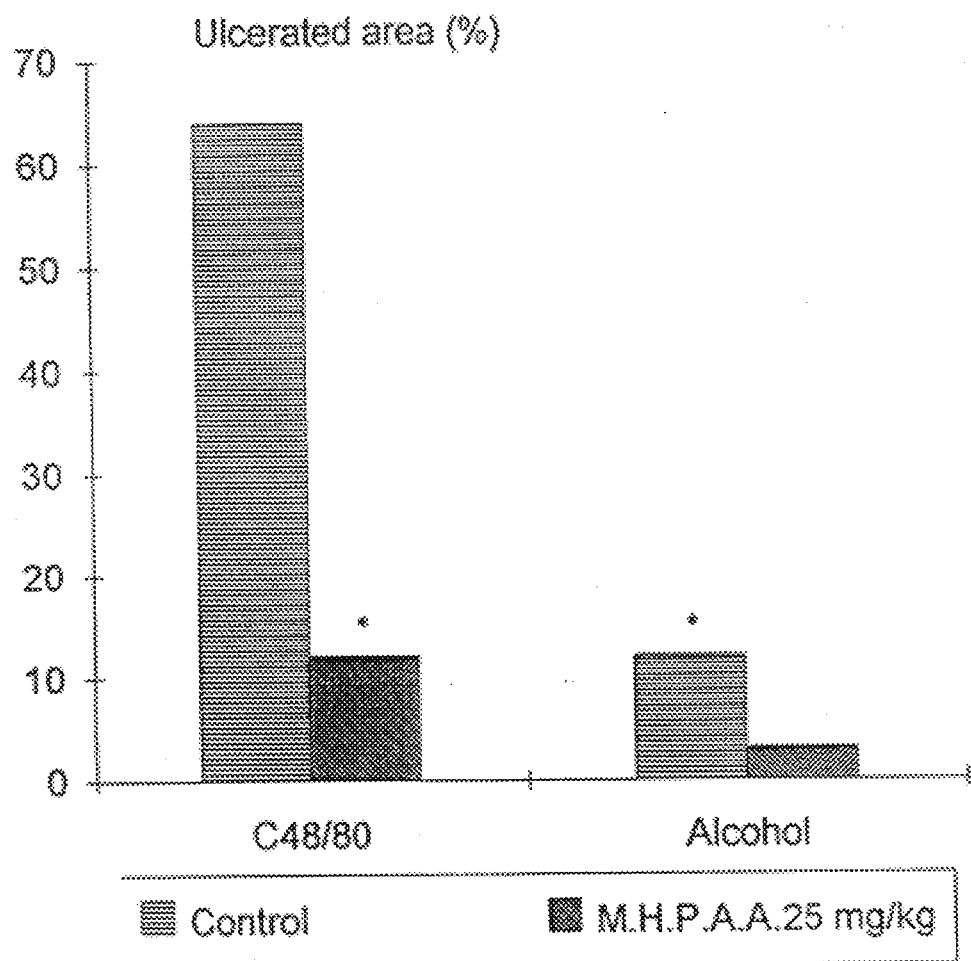

C) Gastric ulcer induced by ASA: Procedure was performed according the same authors referred in the previous paragraph. One hour after treatment with M.H.P.A.A. or vehicle, rats administered orally with ASA (100 mg/kg). Two h later, rats were sacrificed and procedure for gastric ulcer measurement was done as described. Comparisons between control and M.H.P.A.A.-treated groups were performed using the non parametric Mann-Whitney U test. FIG. 19 shows the effect of M.H.P.A.A. on C4880 and alcohol-induced gastric ulcer, p<<0.05 M.H.P.A.A. administered intraperitoneally (25 mg/kg) inhibited significantly the occurrence of gastric ulcer induced by C4880, ethanol and ASA. Moreover, as can be observed in Table 19, M.H.P.A.A. administered orally not only reduces TxB2 but also increase PgI2, thus very significantly reducing TxB2 to PgI2 ratio.

TABLE 19

Effect of M.H.P.A.A. and ASA on the TxB2 levels and 6 keto PgFla in mice serum

| Control | Dosage (mg/kg) | TxB2 (ng/mL) | 6 ketoPgFla (ng/mL) | Index TxB2/6Keto PgFla |
|---|---|---|---|---|
| Control |  | 286 + 16.7 | 1.65 + 0.26 | 173 |
| ASA | 50 | 36.3 + 13.3 ** | (a) 1.12 + 0.41 | 46.5 * |
| M.H.P.A.A. | 180 | 182 + 31.9 ** | (b) 3.91 + 0.4 * | 32.4 ** |
| M.H.P.A.A. + ASA |  | 9.25 + 5.4 ** | (c) 1.57 + 0.16 | 5.8 *** |

* $p < 0.05$;  $p < 0.01$; * $p < 0.001$
a = b = c (Mann Whitney U test)

The inhibition of the TxB2 levels and the increase of PgI2 induced by M.H.P.A.A. could explain the protective effect of this mixture against gastric ulcer. Thus, it is observed a highly significant decrease of the $TxB_2$ to $PgI_2$ ratio when combined treatment of M.H.P.A.A. and ASA is used. Moreover, this mechanism also could supports alcohols mixture effects on the other drug-induced gastric ulcer.

EXAMPLE 21

Forty-five outpatients from both sexes, aged from 25 to 70 years, with Type II hyperlipoproteinemia received, under double blind conditions, M.H.P.A.A. or placebo tablets once a day for 6 weeks (treated patients received M.H.P.A.A. at 5 mg/day). Before and after treatment the following parameters were investigated: bleeding time, platelet count, prothrombine time, antithrombin III activity, lysis time, plasmatic euglobulin fraction, platelet aggregation induced by ADP and malondialdehyde (MDA) concentration.

Table 20 summarizes the data. They show that none of the parameters related with the coagulation process were affected, while a significant difference between group of platelet agreggation-ADP induced was obtained. In addition, a marginally significant reduction of MDA was also observed (p=0.058).

TABLE 20

Effects of M.H.P.A.A. treatment in blood coagulation and platelet aggregation in patients with Type II hyperlipo-proteinemia

|  | time of analysis | Placebo | M.H.P.A.A. (5 mg/day) |
|---|---|---|---|
| Bleeding time | 0 | 2'47" +/− 1'26" | 2'31" +/− 1'24" |
|  | 6 w | 2'10" +/− 1'34" | 2'08" +/− 1'06" |
| Platelet count | 0 | 201.23 +/− 29.98 | 198.13 +/− 39.48 |
|  | 6w | 188.55 +/− 35.99 | 175.33 +/− 40.87 |
| Prothrombine time | 0 | 13.67 +/− 1.80 | 14.43 +/− 4.18 |
|  | 6 w | 13.40 +/− 1.10 | 13.69 +/− 2.25 |
| Fibrinogen | 0 | 2.64 +/− 0.46 | 2.84 +/− 0.54 |
|  | 6 w | 2.81 +/− 0.52 | 2.92 +/− 0.44 |
| Antithrombin III activity | 0 | 79.95 +/− 7.50 | 82.86 +/− 11.97 |
|  | 6 w | 91.78 +/− 9.69 | 93.67 +/− 14.62 |
| Lysis time | 0 | 247.27 +/− 30.10 | 230.43 +/− 48.19 |
|  | 6 w | 248.64 +/− 55.72 | 228.48 +/− 45.39 |
| P.E.F. | 0 | 35.79 +/− 18.18 | 36.93 +/− 20.93 |
|  | 6 w | 47.59 +/− 21.29 | 30.98 +/− 24.19 |
| ADP | 0 | 48.98 +/− 16.28 | 52.27 +/− 24.26 |
|  | 6 w | 56.97 +/− 24.77 | 27.45 +/− 24.81 ++ |
| MDA | 0 | 2.99 +/− 1.75 | 2.45 +/− 2.31 a |
|  | 6 w | 2.79 +/− 1.28 | 1.76 +/− 1.67 | a p = 0.058
++ p < 0.01 (Mann Whitney U test)

We claim:

1. A mixture of higher primary aliphatic alcohols from 24 to 34 carbon atoms comprising 1-tetracosanol, 1-hexacosanol, 1-heptacosanol, 1-octacosanol, 1-nonacosanol, 1-triacontanol, 1-dotriacontanol and 1-tetratriacontanol having by the following quantitative composition:

| 1-tetracosanol | 0.5–1.0% |
|---|---|
| 1-hexacosanol | 5.5–8.5% |
| 1-heptacosanol | 2.0–3.5% |
| 1-octacosanol | 60.0–70.0% |
| 1-nonacosanol | 0.4–1.2% |
| 1-triacontanol | 10.0–15.0% |
| 1-dotriacontanol | 4.0–6.0% |
| 1-tetratriacontanol | 0.4–2.0% | characterized by a combination with acetyl salicylic acid in a quantitative ratio from 20:1 to 1:20.

2. The mixture of higher primary aliphatic alcohols according to claim 1 having the following quantitative composition:

| 1-tetracosanol | 0.80 +/− 0.1% |
|---|---|
| 1-hexacosanol | 6.7 +/− 0.3% |
| 1-heptacosanol | 3.0 +/− 0.3% |
| 1-octacosanol | 65.6 +/− 3.4% |
| 1-nonacosanol | 0.7 +/− 0.1% |
| 1-triacontanol | 12.5 +/− 0.6% |
| 1-dotriacontanol | 5.0 +/− 0.4% |
| 1-tetratriacontanol | 0.8 +/− 0.1% | further comprising acetyl salicylic acid in a quantitative ratio from 20:1 to 1:20.

3. The mixture of higher primary aliphatic alcohols according to claim 1 further comprising acetyl salicylic acid in a quantitative ratio from 10:1 to 1:10.

4. The mixture of higher primary aliphatic alcohols according to claim 2 further comprising acetyl salicylic acid in a quantitative ratio from 10:1 to 1:10.

5. A pharmaceutical formulation comprising the mixture of higher primary aliphatic alcohols constituted by the following quantitative compositions

| 1-tetracosanol | 0.5–1.0% |
|---|---|
| 1-hexacosanol | 5.5–8.5% |
| 1-heptacosanol | 2.6–3.5% |
| 1-octacosanol | 60.0–70.0% |
| 1-nonacosanol | 0.4–1.2% |
| 1-triacontanol | 10.0–15.0% |
| 1-dotriacontanol | 4.0–6.0% |
| 1-tetratriacontanol | 0.4–2.0% | in combination with acetyl salicylic acid in a quantitative ratio from 20:1 to 1:20, and pharmaceutically acceptable excipients.

6. The pharmaceutical formulation of claim 5 in the form of tablets, capsules, microgranules, or granules.

7. The pharmaceutical formulation of claim 5 having acetyl salicylic acid in a quantitative ratio from 10:1 to 1:10.

8. A pharmaceutical formulation comprising a mixture of higher primary aliphatic alcohols constituted by the following quantitative composition:

| 1-tetracosanol | 0.8 +/− 0.1% |
|---|---|
| 1-hexacosanol | 6.7 +/− 0.3% |
| 1-heptacosanol | 3.0 +/− 0.3% |
| 1-octacosanol | 65.6 +/− 3.4% |
| 1-nonacosanol | 0.7 +/− 0.1% |
| 1-triacontanol | 12.5 +/− 0.6% |
| 1-dotriacontanol | 5.0 +/− 0.4% |
| 1-tetratriacontanol | 0.8 +/− 0.1% | further comprising acetyl salicylic acid in a quantitative ratio from 20:1 to 1:20, and pharmaceutically acceptable excipients.

9. The pharmaceutical formulation of claim 8 in the form of tablets, capsules, microgranules, or granules.

10. The pharmaceutical formulation of claim 8, having acetyl salicylic acid in a quantitative ratio from 10:1 to 1:10.

11. A method of using a mixture of higher primary aliphatic alcohols with the following quantitative composition:

| 1-tetracosanol | 0.5–1.0% |
|---|---|
| 1-hexacosanol | 5.5–8.5% |
| 1-heptacosanol | 2.0–3.5% |
| 1-octacosanol | 60.0–70.0% |
| 1-nonacosanol | 0.4–1.2% |
| 1-triacontanol | 10.0–15.0% |
| 1-dotriacontanol | 4.0–6.0% |
| 1-tetratriacontanol | 0.4–2.0% | as antiplatelet agent.

12. A method of using a mixture of higher primary aliphatic alcohols with the following quantitative composition:

| 1-tetracosanol | 0.5–1.0% |
|---|---|
| 1-hexacosanol | 5.5–8.5% |

-continued

| | |
|---|---|
| 1-heptacosanol | 2.0–3.5% |
| 1-octacosanol | 60.0–70.0% |
| 1-nonacosanol | 0.4–1.2% |
| 1-triacontanol | 10.0–15.0% |
| 1-dotriacontanol | 4.0–6.0% |
| 1-tetratriacontanol | 0.4–2.0% | as antithrombotic agent.

13. A method of using a mixture of higher primary aliphatic alcohols with the following quantitative composition

| | |
|---|---|
| 1-tetracosanol | 0.5–1.0% |
| 1-hexacosanol | 5.5–8.5% |
| 1-heptacosanol | 2.0–3.5% |
| 1-octacosanol | 60.0–70.0% |
| 1-nonacosanol | 0.4–1.2% |
| 1-triacontanol | 10.0–15.0% |
| 1-dotriacontanol | 4.0–6.0% |
| 1-tetratriacontanol | 0.4–2.0% | as anti-ischemic agent.

14. A method of using a mixture of higher primary aliphatic alcohols with the following quantitative composition

| | |
|---|---|
| 1-tetracosanol | 0.5–1.0% |
| 1-hexacosanol | 5.5–8.5% |
| 1-heptacosanol | 2.0–3.5% |
| 1-octacosanol | 60.0–70.0% |
| 1-nonacosanol | 0.4–1.2% |
| 1-triacontanol | 10.0–15.0% |
| 1-dotriacontanol | 4.0–6.0% |
| 1-tetratriacontanol | 0.4–2.0% | as protective and/or curative agent against gastric ulcer induced by drugs.

15. A method of using a mixture of higher primary aliphatic alcohols with the following quantitative composition

| | |
|---|---|
| 1-tetracosanol | 0.5–1.0% |
| 1-hexacosanol | 5.5–8.5% |
| 1-heptacosanol | 2.0–3.5% |
| 1-octacosanol | 60.0–70.0% |
| 1-nonacosanol | 0.4–1.2% |
| 1-triacontanol | 10.0–15.0% |
| 1-dotriacontanol | 4.0–6.0% |
| 1-tetratriacontanol | 0.4–2.0% | together with acetyl salicylic acid as an antiplatelet, anti-ischemic or antithrombotic agent.

16. A method of using the mixture of higher primary aliphatic alcohols according to claim 15 wherein said mixture further comprises acetyl salicylic acid in a quantitative ratio from 20:1 to 1:20.

17. A method of using the mixture of higher primary aliphatic alcohols according to claim 16 wherein said mixture further comprises acetyl salicylic acid in a quantitative ratio from 10:1 to 1:10.

18. A method of using a mixture of higher primary aliphatic alcohols with the following quantitative composition

| | |
|---|---|
| 1 - tetracosanol | 0.8 +/– 0.1% |
| 1 - hexacosanol | 6.7 +/– 0.3% |
| 1 - heptacosanol | 3.0 +/– 0.3% |
| 1 - octacosanol | 65.6 +/– 3.4% |
| 1 - nonacosanol | 0.7 +/– 0.1% |
| 1 - triacontanol | 12.5 +/– 0.6% |
| 1 - dotriacontanol | 5.0 +/– 0.4% |
| 1 - tetratriacontanol | 0.8 +/– 0.1% | together with acetyl salicylic acid as antiplatelet, anti-ischemic or antithrombotic agent.

19. A method of using the mixture of higher primary aliphatic alcohols according to claim 18 wherein said mixture further comprises acetyl salicylic acid in a quantitative ratio from 20:1 to 1:20.

20. A method of using the mixture of higher primary aliphatic alcohols according to claim 19 wherein said mixture further comprises acetyl salicylic acid in a quantitative ratio from 10:1 to 1:10.

* * * * *